US006280751B1

(12) United States Patent
Fletcher et al.

(10) Patent No.: US 6,280,751 B1
(45) Date of Patent: Aug. 28, 2001

(54) ESSENTIAL OIL COMPOSITION

(76) Inventors: Jane Clarissa Fletcher; Michael James Hargreaves Riley, both of Hollyhurst, Church Street, Hampton Lucy, CV35 8BD, Warwickshire (GB)

( * ) Notice: Subject to any disclaimer, the term of this patent is extended or adjusted under 35 U.S.C. 154(b) by 0 days.

(21) Appl. No.: 09/380,971

(22) PCT Filed: Mar. 10, 1998

(86) PCT No.: PCT/GB98/00708

§ 371 Date: Nov. 5, 1999

§ 102(e) Date: Nov. 5, 1999

(87) PCT Pub. No.: WO98/40086

PCT Pub. Date: Sep. 17, 1998

(30) Foreign Application Priority Data

Mar. 10, 1997 (GB) .................................................. 9704904

(51) Int. Cl.⁷ ............................ A61K 35/78; A61K 6/00; A61K 9/48; A61K 9/20
(52) U.S. Cl. .................... 424/401; 424/195.18; 424/451; 424/464
(58) Field of Search .............................. 424/195.18, 401, 424/451, 464

(56) References Cited

U.S. PATENT DOCUMENTS

| | | | |
|---|---|---|---|
| 4,918,099 | * 4/1990 | Moon | .................................. 514/453 |
| 5,073,545 | * 12/1991 | Arima et al. | ........................... 514/27 |
| 5,356,811 | 10/1994 | Coats | .................................... 435/267 |
| 5,578,307 | * 11/1996 | Wunderlich et al. | ............. 424/195.1 |

FOREIGN PATENT DOCUMENTS

| | | |
|---|---|---|
| 1130076 | 9/1996 | (CN) . |
| 2555445 | 3/1985 | (FR) . |
| 2250830 | 10/1990 | (JP) . |
| 9136831 | 5/1997 | (JP) . |
| 9227394 | 7/1997 | (JP) . |
| 2001095 | 10/1993 | (RU) . |
| 2001944 | 10/1993 | (RU) . |
| 2053265 | 1/1996 | (RU) . |
| 2055874 | 3/1996 | (RU) . |
| 2066194 | 9/1996 | (RU) . |
| 2080800 | 6/1997 | (RU) . |
| 2085204 | 7/1997 | (RU) . |
| 2092540 | 10/1997 | (RU) . |
| 2092543 | 10/1997 | (RU) . |
| 1468490 | 3/1989 | (SU) . |
| 93/11780 | 6/1993 | (WO) . |

* cited by examiner

Primary Examiner—Thurman K. Page
Assistant Examiner—S. Tran
(74) Attorney, Agent, or Firm—Barnes & Thornburg

(57) ABSTRACT

The application relates to new medicinal and cosmetic compositions comprising essential oils in combination with herbs and/or spices. The compositions may be used orally or topically.

12 Claims, No Drawings

ESSENTIAL OIL COMPOSITION

CROSS-REFERENCES TO RELATED APPLICATIONS

This application is a U.S. national application of international application Ser. No. PCT/GB98/00708 filed Mar. 10, 1998, which claims priority to Great Britain Ser. No. 9704904.3 filed Mar. 10, 1997.

The invention relates to medicinal and cosmetic compositions comprising an essential oil in combination with at least one spice and/or at least one herb. Such compositions may be taken orally or may be absorbed through the skin.

Essential oils have been used for thousands of years in aromatherapy. The ancient Chinese are generally acknowledged as the founders of aromatherapy, but it is more than likely that quite early in the history of civilisation man had realised that certain aromatic plants could help restore his health. Aromatic substances were also used by the ancient Egyptians and Ancient Greeks as medicinal perfumes.

In the 10th century the Arabs were extracting essential oils from aromatic plants and using them medicinally. The Knights of the Crusades brought aromatic essences and waters back to Europe from the Middle East and they became so popular that perfume began to be manufactured and was well established by the end of the 12th century. The importance of aromatic plants for other purposes was realised early. When the bubonic plague reached England around the middle of the 14th century, fires were ordered in the streets at night, burning aromatic frankincense and pine; indoors, incense and perfumed candles were burnt to combat infection and disguise the stench of death; pomanders made from aromatic gums and resins were worn on ribbons round the neck to protect the wearers from the dreaded Black Death.

By the turn of the 18th century essential oils were widely used in medicinal preparations and Salmon's dispensary of 1896 contains recipes for numerous aromatic remedies. In the 19th century, essential oils were subjected to more scientific investigation, and it was discovered that some of them could be synthesised from other materials. As it is always quicker and cheaper to produce the laboratory versions than natural plant extracts, true essential oils began to fall from favour. Today, many of our medicines and perfumes contain so-called essential oils, though often they are mere imitations; while synthetics may smell like the real thing, they do no possess the same therapeutic properties.

Essential Oils

Essential oils are highly scented droplets found in minute quantities in the flowers, stems, leaves, roots and barks of aromatic plants. They are not true oils in the manner of lubricant vegetable oils, but highly fluid and exceptionally volatile.

Essential oils are complex mixtures of different organic molecules—terpenes, alcohols, esters, aldehydes, ketones and phenols. Synthetic oils are usually made from one or more of the constituents predominant within a particular essential oil; menthol, for example, often substitutes for mint and eucalyptol for eucalyptus. However, there are sound reasons for believing that it is the interaction between each and every component that gives an essential oil its particular character and unique therapeutic properties.

The chemical composition of an oil is related to the time of day, the month or the season. Jasmine develops a strongly scented indole molecule at midnight when it is particularly intoxicating, and it is important to gather the petals at exactly the right moment. There are good years and bad years for essential oils as there are with wines. Some commercial producers have discovered that they can improve the quality of a poor yield by adding certain components and that an expensive oil like rosemary can be adulterated, without altering its aroma, by adding 30–40% of camphor which is considerably cheaper for the perfume industry. Such adulteration may be commercially acceptable but it might well alter the therapeutic properties of the oil. It is important to try to ensure that essential oils come from reputable sources and are as pure as possible.

Experts recognise an essential oil by its aroma and check its composition by a process called Gas Liquid Chromatography. Colour can also be an indicator; eucalyptus is colourless, chamomile varies from white to blue and others, like basil and sandalwood (both light greenish-yellow), are in pastel shades. Yet others are richly pigmented, like jasmine, a deep reddish-brown, patchouli, brown, and rose, orange-red.

Extraction of the Oils

Essential oils may be extracted from plants in a number of ways. One of the oldest methods is distillation, practised in ancient Persia, Turkey and India thousands of years ago. The Egyptians were preparing essence of cedarwoods for embalming and other purposes around 2000 BC; the wood was heated in a clay vessel covered by a screen of woollen fibres through which the steam had to pass. The essence was obtained by squeezing out the impregnated wool.

The Arabs are credited with having popularised distillation in the late 10th century. They began with extract of rose petals then experimented with other aromatic materials. Today, distillation remains the most commonly used means of extracting essential oils.

Other methods include enfleurage, often used for delicate petals like jasmine and tuberose; maceration, for tougher flowers and leaves, roots and bark; solvent extraction, the preferred method for gums and resins like myrrh and galbanum; and hand expression, chiefly employed for squeezing the highly aromatic oils from thick-skinned citrus fruit like oranges, tangerines and lemons.

The Properties and Uses of Essential Oils

Essential oils possess numerous properties which make them useful for treating many of our most common health and beauty troubles.

Professor Paolo Rovesti, Director of the Instituto Derivati Vegetali in Milan, has studied the effect of essential oils on the psyche and found that they can be useful in the treatment of anxiety and depression. He recommends ylang—ylang, citrus oils, jasmine, basil, patchouli and peppermint for treating general depression, geranium, lavender and bergamot for treating fear and anxiety, and peppermint, rose and carnation for improving concentration and eliminating lethargy. Sprayed into the air, these oils also have immediate and long-lasting effects.

The reasons for these reactions are as yet unclear, but it is known that odour molecules are perceived by thousands of tiny nerve cells in the nose and that each of these nerves is connected to that part of the brain which is concerned with emotional drives, creativity and sexual behaviour. This could explain why certain perfumes make us feel happy, why some essences, like jasmine and rose, have a reputation for being aphrodisiac and why unpleasant smells, like petrol fumes, can induce depression. While pure essential oils appear to have a positive influence on the psyche, it is doubtful that synthetic ones work in the same way.

Spices are conventionally used as flavourings in, for example, Indian or Thai dishes. Spices are usually the dried, aromatic parts of plants, generally the seeds, berries, roots, pods and sometimes leaves and flesh, which mainly, but not invariably, grow in hot countries.

The medicinal uses of spices in the past were often indistinguishable from their culinary uses, particularly so in mediaeval times, when apothecaries prescribed herbs and spices not merely for digestive problems, but for all types of ailments. Hot spices, such as pepper, were regarded as an appetite stimulant and a digestive aid; asafoetida, now known only in Indian cookery, was used by the Romans as a healing ointment, an antidote for snake bites, and an cure for gout, cramps, pleurisy, and tetanus; spiced salts were made with ginger, pepper, cumin, thyme and celery seed which were good for the digestion, promoting regularity and preventing 11 sorts of illnesses, plagues and chills; and citron seeds were given to pregnant women to relieve nausea. Roman and mediaeval writers also believed the fennel helped to promote and restore good vision and it was at one time a cure for obesity.

Chinese herbal medicine has been known in China for several thousands of years. Only recently, however, has it become recognised in the West that Chinese herbs may be used to treat medical conditions.

The inventors have unexpectedly found that it is possible to combine essential oils with naturally occurring spices and/or herbs to produce medicinal compositions which may be taken orally or which may be directly absorbed through the skin. Compositions of the invention may be used to treat a surprising range of illnesses.

Such compositions are especially important with the move by many members of the public towards more "natural" treatments, which do not use artificial medicines.

Accordingly a first aspect of the invention provides a medicinal or cosmetic composition comprising at least one essential oil in combination with at least one spice and/or herb. Preferably the spice is an "Indian spice" as defined herein. The herb is preferably a "Chinese herb" as defined herein.

Preferably the composition comprises an Aloe vera extract. This is the preferred delivery vehicle for the essential oil and spice and/or herb. It is preferred since it is readily accepted by the body and has not been found to produce allergic reactions or side effects. Preferably the extract is concentrated.

The composition may comprise a honey product such as royal jelly or bee propolis. Royal jelly and bee propolis have been used for many years to treat a wide range of conditions and as nutrient supplements.

Indian brandee may also be incorporated with the composition. Indian brandee has been used for many years as to relieve flatulence and colic. Its main ingredients are rhubarb tincture, capiscum tincture, ethanol, cochineal and methyl hydroxybenzoate.

The composition may also comprise one or more flavourings, such as blackcurrant concentrate, vitamins, amino acids and minerals. Examples of vitamins include Vitamin C and Vitamins E and D, which may be in the form of alpha-tocopherol. Inositol, pepsin, selenium methionine, soya isolate, trace mineral clay, whey protein, zinc amino acid chelate and individual amino acids such as lysine may be used. Enzymes, such as plant extracts comprising enzymes may also be incorporated.

The essential oils, spices, herbs and vitamins and amino acids preferably used within the invention are shown in Tables 1 to 4.

Preferably the compositions comprise one or more essential oils selected from:

(a) bergamot, chamomile german, chamomile maroc, chamomile roman, cinnamon zeylanicum, clove buds, eucalyptus globulus, frankincense, fennel, hyssop, juniper, lemon grass, mountain savoury, niaouli, red thyme, rosemary, rose geranium, tagestes and ylang ylang.

The compositions may comprise one or more Chinese herbs selected from:

(b) acacia catechu, acanthopanax gracilistylus, caesalpinia sappan and epimedium spinosa.

Preferably the compositions comprise one or more spices selected from:

(c) asapoetidia, coconut, coriander, fenugreek and horseradish.

Preferably the composition comprises all of the oils, herbs and spices from lists (a), (b) and (c). This combination has been found to especially improve the effectiveness of the compositions.

Compositions of the invention may be used in combination with alternative methods of treatment such as aromatherapy, Bach flowers therapy, reflexology, acupuncture and/or the Alexander technique, all of which are known in the art.

The invention may be used orally or topically. Accordingly the invention preferably provides tablets or capsules comprising the compositions of the invention for oral administration.

Compositions for topical administration comprising the compositions according to the invention are also provided.

The invention further provides the use of a medicinal composition according to the invention for the treatment of disease or physical disability or sports injuries, or for the build up and maintenance of the immune system, or for the protection against disease or pollution.

The use of cosmetic formulations according to the invention are also provided for skin care and/or weight management. aromatherapy and/or reflexology and/or physiotherapy to produce enhanced results.

Essential oils are typically extracted by steam distillation, expression (hard pressing) or maceration, as indicated in Table 1. Such techniques are well known in the art.

Spices are preferably selected from Table 2.

Chinese Herbs

Herbs and Their Properties

In China the herbs used are gathered from the wild by hand. The best ones grow far from human habitation, and the herbalists who gather them will also be botanists, explorers, climbers and environmentalists. They need to be able to identify the relevant herb in all stages of its development, know where the finest ones grow, be able to get to the plants even when they grow in highly inaccessible places, know how much they can take without threatening a particular species, and always be on

TABLE 1

| ESSENTIAL OILS |
|---|
| Aniseed |
| Basil |
| Benzoin |
| Bergamot |
| Black Pepper |
| Camphor |
| Carrot |
| Cedarwood |
| Chamomile German |
| Chamomile Maroc |
| Chamomile Roman |
| Cinnamon Leaf |

TABLE 1-continued

ESSENTIAL OILS

Clove Buds
Cypress
Dill
Eucalyptus Globulus
Fatigue
Fennel
Frankincense
Ginger
Grand Fir
Grapefruit
Grapeseed
Hazel
Hyssop
Jojoba
Juniper
Juniper Berry
Lavender
Lemon
Lemon Grass
Melissa
Mountain Savoury
Myrtle Red
Neroli
Niaouli
Patchouli
Peppermint
Pine
Red Myrtle
Rescue Remedy
Rose Geranium
Rosemary
Sandlewood
Spanish Marjoram
Sweet Marjoram
Sweet Thyme
Tagestes
Tea Tree
Thyme Red
Thyme Sweet
Ylang Ylang

TABLE 2

SPICES

Allspice
Allspice Ground
Anise Star
Aniseed
Arrowroot
Arrowroot Ground
Asafoetidia
Caraway Ground
Cardamom
Cardamom Seeds
Carob
Cassia
Cassia Bark
Cayenne Pepper
Celery Salt
Chilli
Chilli Powder
Cinnamon
Cinnamon Ground
Cinnamon Sugar
Cloves
Cloves Ground
Coconut Cream Block
Coconut Ground
Coconut Powder
Coriander
Coriander Ground
Cream of Tartar
Cumin

TABLE 2-continued

SPICES

Dill
Dlll Seeds
Dutch Caraway
Fennel
Fennel Powder
Fenugreek
Fenugreek Powder
Garlic
Ginger
Horseradish
Horseredish Ribbled
Juniper Berries
Laos
Laos Powder
Lemon Grass
Mace
Mace Ground
Mango Powder
Mixed Spices
Mixed Spices - Sweet
Mushroom
Mustard Seed Black
Mustard Seed Yellow
Nutmeg
Nutmeg Powder
Onion
Orris Root
Paprika - Sweet
Slippery Elm
Tamarind Block
Tumeric the look-out for new sources and new species.

They are mostly imported from Hong Kong, although some come from mainland China via Beijing and Shanghai. Increasingly, as China opens its doors to the West, better access will be granted for importing herbs.

Some herbalists import their herbs directly, while others purchase them from Chinese herbal cash and carry stores in the West or from mail order suppliers.

Examples of Chinese herbs which may be used in the invention are listed in Table 3.

Preservation

Once the herbs have been collected from the wild they need to be treated so that they will keep their essential qualities during storage. They are always washed and dried. The method of drying varies depending on the particular herb and what it is going to be used for. They may be sun-dried or dried in a clay oven, alone or with other herbs. Sometimes they are dried with minerals such as sulphur, which bleaches them and also acts as

HERBS

Ba Ji Tian
Bai Dau Kou
Bai Gou
Bai Guo Ye (Ginkgo)
Bai He
Bai Ji Tian
Bai Jiang Cao
Bai Zhi
Bai Zhu
Ban Xia
Bi Ji Tian
Bo He
Bladderwrack
*Boswellia Serrata*
Bu Gu Zhi

HERBS -continued

Cang Er Zi
Chal Hu
*Chamaelirium Lurea* (False Unicorn)
Chan Tiu
Che Qian Cao
Che Qian Zi
Che Quian Cao
Chen Xiang
Chi Shao Yao
Chuan Lian Zi
Da Huang
Da Zao
Dan Shen
Dang Gui (Dong Quai)
Dang Shen
Du Zhong
*Echinacaea Angustifolia*
Er Cha
Fan Xie Ye (Senna)
Fu Ling
Fu Pen Zi
Gao Ben
*Garcinia Cambogia*
Ge Gen
Gou Qi Zi (Lycium)
Gou Teng
Guaiacum Wood
Gui Ban
Guo Teng
Guo Ye (Ginkgo)
He Zi
Horsetail
Hu Huang Lian
Hu Po
Hua Jiao
Huai Jiao Zi
Huang Lian
Huang Qi
Huo Ma Ren
Ji Xue Feng
Jiang Can
Jie Geng
Jin Quian Cao
Jin Yin Hua
Jin Ying Zi
Lian Zi
Lian Zi (Red)
Long Yan Rou
Lu Jiao Shuang
Ma Dou Ling
Mai Men Dong
Mai Ya
Man Jing Zi
Mao Zhao Cao (Cats Claw)
Mate Leaf
Mexican Yam Root
Milk Thistle Seed
Mu Dan Pi
Mu Hu Die
Mu Li
Mu Tong
Niu Bang Zi
Ou Jie
Qiang Huo
Rou Cong Rong
*Salix Alba* (White Willow)
Sang Ye
Shan Zha
Shen Jin Cao
Sheng Ma
Shiu Niu Jiao Si
Shu Di Huang
*Spirulina*
Su Mu
Su Zi (Zi Su Zi)

HERBS -continued

Suan Zao Ren
Tian Ma
Tian Nan Xing
Ting Li Zi
Wang Bu Liu Xing Guo
Wu Bei Zi
Wu Jia Pi
Wu Yao
Xian He Cao
Xing Ren
Yan Hu Suo
Yang Rong Wan
Ye Ju Hua
Ye Tu Hua
Yi Mu Cao
Yin Yang Huo
Yohimbe
Zhen Zhu Mu
Zhi Mu
Zhi Zi a preservative. Occasionally you may hear of herbs being treated. This means that, after drying, they are stir-fried with angelica and milk vetch to enhance their properties. Some may also be buried in the ground to absorb moisture, or cooked in a clay pot with rice wine or honey to increase their potency.

Cutting up Herbs

Before or after they have been dried, the herbs will need to be cut up using a herb chopper. When this is done depends on the herb and its eventual usage. There are several ways of cutting herbs. Large roots are often sliced across at 90 degrees, which gives them a round cross-section, while smaller ones are cut at an angle to give a larger surface area. Some herbs are chopped very finely and compressed into a cake.

Some herbs have to be ground to a powder and this is done using a mortar and pestle with a lid, to avoid the loss of powder during crushing.

Storage

Traditionally, herbs would be stored in clay pots after preservation and cutting up. The shape of the clay pots and whether they were covered or uncovered depended on the herbs. The Chinese have always used clay pots, because clay was the simplest and cheapest material to get hold of and also because, when glazed and therefore non-absorbent, it helped to keep the properties of the herbs intact.

Modern herbalists increasingly use glass jars and bottles for herb storage, but still rely on wooden drawers for the bulk of their stocks because this is the easiest and most convenient method of dispensing them. These drawers are rarely labelled, as the herbalist is completely familiar with their contents. Since the drawers are arranged according to meridians and properties it would be hard for the herbalist to make a mistake that would result in a herb of a totally different type being dispensed.

Freshness of Stocks

However the herbs are stored, herbalists will check them periodically for mould and other signs of decay.

Herbs may need to be retreated—that is, washed and boiled, redried and, where necessary, freshly treated with angelica again in the same way that fresh herbs are.

Weighing Herbs

Because it is so expensive, ginseng is weighed in very sensitive scales which have divisions of 0.1 of a gram.

Other herbs do not need quite such accurate scales, and larger ones can be used. These are accurate to within approximately 3 grams. Both sorts of scales are used by holding one of the strings near the pan and adjusting the weight on the rod.

Metric weights have been used for convenience, but Chinese herbalists use Chinese weights. Their names and metric equivalents are given below.

| | | |
|---|---|---|
| 1 fan = | | 0.3 grams approx |
| 10 fan = | 1 qin = | 3 grams approx |
| 10 qin = | 1 lian = | 30 grams approx |
| 16 lian = | 1 jin = | 480 grams approx |

Whenever scales are used, the weight given is always that of the herb before any stir-frying which may be specified on the prescription. The herbs may be fried in honey, water or rice wine, or 'burned' until black in a red-hot wok. These treatments naturally change the weight of the herb, and it is not unknown for patients to weight their herbs afterwards and mistakenly complain that they have been short-changed by the herbalist.

Boiling and Steaming

As soon as possible after collection, the herbs are boiled in clay pots. These come in a variety of shapes and sizes much like Western saucepans. It used to be traditional to throw away all pots used in medicinal preparations on the Chinese New Year's Eve. But few herbalists in the West can afford to do this now, especially since some of the decorated pots are extremely expensive.

Steam pots are used a lot for medicinal foods. The ingredients are added to the pot, after which both lids are put on and fastened by a string which passes through the handles. The pot is then placed in a larger pot of boiling water. The herbs and other ingredients are gently cooked by the rising steam without losing any valuable elements which might otherwise be boiled out.

Properties of Commonly Used Chinese Herbs

In the following lists the Chinese name has been used, along with the botanical name and the Western common name where possible. (Some Chinese herbs are not native to the West and have no corresponding Western name so in these cases the literal English translation has often been included.) Most of the herbs described here can be used in their fresh state, but they can all be ordered as dried herbs. Dosages given are standard ones from which herbalists would raise or lower according to the individual. It is interesting to note that many of the Chinese names have isuffixes denoting parts of the plant, for example: hua/flower; pi/cortex or peel; ren/seeds; ye/leaf; zi/fruit or seeds. The dosage refers to the total dose over the course duration.

| | | |
|---|---|---|
| Bai Shao | *Paeonia lactiflora, P. obovata* | White peony root |
| Part used: | root, sliced | |
| Meridian: | liver | |
| Taste: | sweet | |
| Usage: | for abdominal pains after childbirth combine with Dang Gui (*Angelica sinensis*/Chinese angelica), Chuan Xiong (*Ligustrum wallichii*/Szechuan lovage root) and Hong Hua (*Carthamus tinctorius*/safflower). | |
| Dosage: | 6–15 g | |
| Note: | Do not use with black false hellebore (*Veratrum nigrum*) | |
| Bai Zhu | *Atractylodes macrocephala* | Attractylodes |
| Part used: | root | |
| Meridians: | spleen, stomach | |
| Taste: | bitter-sweet | |
| Usage: | to correct mischannelling of qi at the spleen and stomach. Used to treat loss of appetite, extended tight abdomen, vomiting and bowel disorders. It is safe to use during pregnancy. | |
| Dosage: | 4.5–9 g | |
| Gan Cao | *Glycyrrhiza uralensis, G. glabra* | Liquorice |
| Part used: | root | |
| Meridians: | all | |
| Taste: | sweet | |
| Usage: | one of the most frequently used Chinese herbs. It can be used on its own to assist the spleen, dispel heat and restore qi. It is used to treat sore throats and to relieve food poisoning. It is most often used with other herbs to moderate their effects. It is also used to alleviate any uncomfortable side-effects which may be felt after taking other medicinal herbs. | |
| Dosage: | 1.5–9 g | |
| Gou Qi Zi | *Lycium chinense* | Lycium |
| Part used: | seed | |
| Meridians: | liver, kidneys | |
| Taste: | sweet | |
| Usage: | to strengthen shen and kidneys, and to improve eyesight, used with Sheng Di Huang (*Rehmania glutinosa*/Chinese foxglove root), Ju Hua (*Chrysanthemum morifolium*/chrysanthemum) and Shan Zhu Yu (*Comus officinalis*/fruit of Asiatic comelian cherry). Used with Sheng Di Huang (*Rehmania glutinosa*) and Tian Men Dong (*Asparagus cochinchinensis*/asparagus root) to treat deficient liver and/or kidneys as well as tinnitus, dizziness and weakness of the knees, and for the prevention of wet dreams. | |

-continued

| | | |
|---|---|---|
| Dosage: | 6–12 g | |
| Gou Teng | *Nauclea rhyncholphylla* | also (Unicaria) |
| Part used: | thorn | |
| Meridians: | heart, liver | |
| Taste: | sweet | |
| Usage: | to stop convulsions, tics and spasms used with Tian Ma (*Gastrodia elata*/Gastrodia rhizome). For the treatment of red eyes caused by headaches used with Ju Hua (*Chrysanthemum morifolium*/chrysanthemum), Sang Ye (*Morus alba*/white mulberry leaves) and Bo He (*Mentha arvensis*/mint). It does not need boiling. | |
| Dosage: | 6–12 g | |
| Gui Zhi | *Cinnamomum cassia* | Cinnamon twigs |
| Part used: | bark | |
| Meridians: | heart, lungs, bladder | |
| Taste: | sweet | |
| Usage: | used in combination with Ma Huang (*Ephedra sinical*/Ephedra) if the patient does not sweat; if they do, given with peeled Chi Shao (*Paeonia veitchii*/red peony root). Used in combination with Qiang Huo (*Notopterygium incisum*) to relieve pain in joints, especially arthritis. Used with Dang Gui (*Angelica sinensis*/Chinese angelica) or Chuan Xiong (*Ligustrum wallichii*/Szechuan lovage root) to treat period pains and menstrual irregularity. | |
| Dosage: | 3–9 g (slightly more if used for arthritis) | |
| Note: | Avoid during pregnancy | |
| Huang Qi | *Astragalus membranaceus* | Milk vetch |
| Part used: | root, sliced, either raw or stir-fired in honey | |
| Meridians: | lungs, spleen | |
| Taste: | sweet | |
| Usage: | given as a tonic to patients recovering from illness or feeling tired and weak. Can be used in conjunction with ginseng. This is one of most commonly prescribed herbs in Chinese medicine, and symptoms which would point to its use include loss of appetite, coldness, shortness of breath and a tendency to sweat a lot. | |
| Dosage: | 9–30 g | |
| Huang Qin | *Scutellaria baicalensis* | Baical skullcap root |
| Part used: | root, raw or stir-fried in rice wine | |
| Meridians: | gall bladder, small intestine, lungs, large intestine, spleen | |
| Taste: | bitter | |
| Usage: | for throat pain used with Lian Qiao, (*Forsythia suspensa*/forsythia fruit) and Jin Yin Hua (*Linicera japonica*/honeysuckle flower). For relieving high blood pressure used with Ju Hua (*Chrysanthemum morifolium*/chrysanthemum) and Gou Teng (*Nauclea rhyncholphylla*). | |
| Dosage: | 3–10 g | |
| Jing Jie | *Schizonepeta tenuifolia* | |
| Part used: | seeds | |
| Meridians: | none specific | |
| Taste: | tangy | |
| Usage: | to stop swellings and as an excellent painkiller. Used more than any other herb for the treatment of arthritis. Fried until very dark in colour it is used to stop bleeding, especially from haemorrhoids. | |
| Dosage: | 3–9 g | |
| Ma Huang | *Ephedra sinica* | Ephedra |
| Part used: | stalk | |
| Meridians: | bladder, lungs | |
| Taste: | tangy | |
| Usage: | used in combination with Gui Zhi (*Cinnamomum cassia*/cinnamon) to aid sweating. Stir-fried in honey and apricot kernels, restores the function of the lungs and suppresses asthma, especially with coughing. Used with Sheng Jiang (*Zingiber officinale*/fresh ginger rhizome (root) and Bai Zhu (*Atractylodes macrocephala*) to reduce swelling. | |
| Dosage: | 3–9 g | |
| Note: | not suitable for patients who suffer from insomnia or high blood pressure. Not to be used by patients who are already sweating. | |
| Mai Men Dong | *Ophiopogon japonicus* | 'Lush winter wheat' |
| Part used: | root nodules, used raw and pressed flat | |
| Meridians: | stomach, lungs, heart | |
| Taste: | bitter | |
| Usage: | to restore yin. Used with Ban Xia (*Pinellia ternata*/'Half summer') and liquorice for coughs and dry throat. Used with Sheng Di Huang (*Rehmania glutinosa*/Chinese foxglove root), | |

-continued

| | | |
|---|---|---|
| | Xuan Shen (*Scrophularia Ningpoensis*/Ningpo figwort root), Huang Lian (*Coptis chinensis*/golden thread) and Dan Shen (*Salvia miltiorrhiza*/'Scarlet root') for insomnia. | |
| Dosage: | 6–12 g | |
| Mu Dan Pi | *Paeonia suffruticosa* | Tree peony |
| Part used: | bark | |
| Meridians: | kidneys, liver, heart | |
| Taste: | bitter | |
| Usage: | to lower high blood pressure, used with Ju Hua (*Chrysanthemum morifolium*/chrysanthemum) and Jin Yin Hua (*Lonicera japonica*/honeysuckle flower). For menstrual disorders, used with Chai Hu (*Bupleurum chinense*/thorowax) and Dan Gui (*Angelica sinensis*/Chinese angelica). To stop bleeding in internal wounds, dry-fried until dark and given with Hong Hua (*Carthamus tinctorius*/safflower). For period pain, raw slices given with Gui Zhi (*Cinnamomum cassia*/cinnamon) and Hu Tao Ren (*Juglans regia*/walnut). To stimulate the production of blood and to disperse bruises, used fried in rice wine with cinnamon and walnuts. | |
| Dosage: | 6–12 g | |
| Note: | not suitable for use during pregnancy | |
| Qing Hao | *Artemisia annua, A. apiacea* | Wormwood |
| Part used: | leaves | |
| Meridians: | liver, gall bladder | |
| Taste: | bitter, but with a very pleasant smell | |
| Usage: | for the treatment of burns and minor skin disorders, fresh leaves are crushed and applied externally. For the treatment of malaria, used with Huang Qin (*Scutellaria baicalensis*/Baical skullcap root). Ban Xia (*Pinellia ternata*) and *Maronta arundinacea* (arrowroot). | |
| Dosage: | 20–40 g for malaria, 6–15 g for skin applications | |
| Note: | this herb responds best to rapid, short boiling | |
| San Qi | *Panx notoginseng* | Pseudoginseng root |
| Part used | whole plant (it is similar to ginseng) | |
| Meridians: | kidneys, liver | |
| Taste: | bitter | |
| Usage: | to disperse buises, relieve swellings and stop haemorrhaging, and for general relief of pain. | |
| Dosage: | for wounds and pain 1–1.5 g powder three times a day; for cardian arrest 1.5 g twice a day in equal proportions with ginseng | |
| Shan Zhu Yu | *Cornus officinalis* | Cornelian Asiatic cherry |
| Part used: | flesh of fruit | |
| Meridians: | liver, kidneys | |
| Taste: | bitter-sour | |
| Usage: | used in the treatment of abnormally heavy menstruation. Used with ginseng to treat heavy sweating accompanied by exhaustion. | |
| Dosage: | 4.5–9 g | |
| Shi Chang Pu | *Acorius gramineus* | Sweetflag |
| Part used: | root | |
| Meridians: | heart, spleen, stomach | |
| Taste: | tangy | |
| Usage: | for excess tan (mucus). Used with Zhi Zi (*Gardenia jasminoides*/Cape jasmine), young bamboo leaves and extracted ginger juice for treating delirium. To treat tinnitus and amnesia, given with Fu Ling (*Poria cocos*/hoelen) and Yuan Zhi (*Polygala tenuifolia*/root of Chinese Senega). For loss of appetite, given with Huo Xiang (*Agastache rugosa*/Patchouli), Huo Po (*Magnolia officinalis*/magnolia) and Chen Pi (*Citrus reticulata*/tangerine peel). | |
| Dosage: | 3–9 g | |
| Shu Di Huang | *Rehmania glutinosa* | Root of Chinese foxglove cooked in wine |
| Part used: | root (oven dried or frsh) | |
| Meridians | liver, kidneys, heart | |
| Taste: | sweet | |
| Usage: | a) to relieve cold in the blood. Used with Xuan Shen (*Scrophularia ningpoensis*/Ningpo figwort) to reduce high body temperature, dry mouth and red tongue. Given with He Ye (*Nelumbo necifera*/lotus leaves) and Qian Cao Gen (*Rubia cordifolia*/madder root) for blood in vomit or urine. Used with Mu Dan Pi (*Paeonia suffruticosa*/cortex of tree peony root) for macula or dark spots on the skin. To treat thirst associated with diabetes, used with Bi Xie Xu Duan (*Dioscorea batatas*/Chinese yam) and Di Gu Pi (*Lycium chinense*/Chinese wolfberry). | |

|  |  |  |
|---|---|---|
|  | b) Used dried, then fried in rice wine until dark, for restoration of the blood, weakness of the knees, menstrual disorders and tinnitus. |  |
| Dosage: | a) 9–30 g (double if fresh), b) 9–15 g |  |
| Tian Ma | *Gastrodia elata* | Gastrodia rhizome |
| Part used: | tuber |  |
| Meridian: | liver |  |
| Taste: | sweet |  |
| Usage: | to clear collateral channels and to relieve rheumatic pain, given with Jin Yin Hua (*Lonicera japonica*/honeysuckle flower) and Huai Niu Xi (*Achyranthes bidentata*/'Ox knee'). Given with Ban Xia (*Pinellia ternata*/'Half summer') and Bai Zhu (*Atractylodes macrocephala*) in the treatment of migraine, eye disorders and dizziness. Excellent for women suffering headaches, especially after childbirth. |  |
| Dosage: | 3–9 g boiled inwater, 1–1.5 g as a powder |  |
| Tian Men Dong | *Asparagus cochinchinensis* | Tuber of Chinese asparagus |
| Part used: | root, raw and sliced |  |
| Meridians: | lungs, kidneys |  |
| Taste: | bitter-sweet |  |
| Purpose: | to restore deficient yin. Dispels heat and strengthens the kidneys and lungs. |  |
| Usage: | to treat a dry cough with little mucus, or coughing up of blood, use with Mai Men Dong (*Ophiopogon japonicus*/'Lush winter wheat') and Bei Mu (*Fritillaria verticillata*/fritillaria bulb). For use in the treatment of whooping cough with Mai Men Dong (*Ophiopogon japonicus*/'Lush winter wheat') and Bai Bu (*Stemona sessilifolia*/stemona root). |  |
| Dosage: | 6–12 g |  |
| Tu Si Zi | *Cuscuta chinensis* | Dodder seeds |
| Part used: | seeds, boiled and crushed, sometimes in cake form |  |
| Meridians: | kidneys, lungs |  |
| Taste: | sweet |  |
| Purpose: | to treat deficient yang in the kidneys, which causes frequent urination. Also used to prevent miscarriages and to help restore the function of the kidneys and menstrual cycle |  |
| Dosage: | 6–12 g |  |
| Wu Wei Zi | *Schizandra chinensis, S. spenanthera* | Schisandra fruit |
|  | The Chinese name means 'the fruit which has five tastes'. It has two forms, northern (*S. Chinensis*) and southern (*S. sphenanthera*). |  |
| Part used: | fruit, raw or steamed with vinegar or rice wine |  |
| Meridians: | kidneys, heart, lungs |  |
| Taste: | sour |  |
| Usage: | for coughs caused by weakness of the lungs, sometimes in combination with ginseng. Use with Mai Men Dong (*Ophiopogon japonicus*/'Lush winter wheat') to treat patients who sweat, have a dry mouth, tire easily and are depressed. |  |
| Dosage: | 1.5–6 g |  |
| Xin Yi Hua | *Magnolia liliflora* | Magnolia flower |
| Part used: | flower |  |
| Meridians: | none specific |  |
| Taste: | tangy |  |
| Usage: | for the treatment of rhinitis and nasosinusitis. Clears running nose and headaches. |  |
| Dosage: | 1–3 g |  |
| Yin Yang Huo | *Eimedium brevicornum, E. grandiflorum, E. sagittatum* | 'Licentious goat wort' |
| Part used: | the whole plant apart from the root |  |
| Meridians: | liver, kidneys |  |
| Taste: | sweet |  |
| Usage: | used to treat high blood pressure in elderly women, impotence and paralysis of the lower limbs. |  |
| Dosage: | 3–9 g |  |
| Yu Xing Cao | *Houttuynia cordata* | 'Fishy smelling herb' |
| Part used: | whole herb |  |
| Meridians: | kidneys, lungs |  |
| Taste: | sweet with a fishy odour, hence it is also know as the smelly fishy plant |  |
| Usage: | the treatment of lung and kidney disorders. |  |
| Dosage: | 9–30 g |  |
| Yuan Zhi | *Polygala tenuifolia* | Root of Chinese senega |
| Part used: | root, chopped and treated with liquorice |  |
| Meridians: | lungs, heart, kidneys |  |
| Taste: | bitter |  |
| Usage: | for treatment of irritability, insomnia and depression. |  |
| Dosage: | 3–9 g |  |
| Zi Su Ye | *Perilla frutescens* | Perilla leaf |

-continued

| | |
|---|---|
| Part used: | leaves |
| Meridians: | spleen, lungs |
| Taste: | sweet |
| Usage: | to promote ch'i, to relieve pain and tightness in the abdomen, to cancel out the effects of food poisoning (especially when caused by seafood), to ease vomiting and diarrhoea. |
| Dosage: | 6–12 g |

Also part of the herbalist's traditional repertoire will be such well-known herbs as ginseng, garlic and ginger. Ginseng (*Panax ginseng*) is the dried root of the Ren Shen plant which is grown mainly in Japan and Korea. Its main uses are to help strengthen weak bodies and to help patients recovering after illness. It is used extensively as a nutritive and restorative tonic and to treat impotence, neurasthenia, spermatorrhoea, anaemia, senility, uterine disorders and nephritis.

Ginger is the fresh root of *Zingiber officianale* (Gan Jiang) and is used mainly as a stomach restorative. It is used in the treatment of nausea and vomiting as well as diarrhoea, rheumatism, abdominal and spleen ache and sometimes for strider—obstructed breathing.

Garlic (*Allium sativum*) known as Xie Bai to the Chinese, is used to thin the blood. It is known to reduce blood cholesterol, prevent heart disease, aid digestion and to lower blood pressure.

The preferred form of the vitamins and amino acids are shown in Table 4. "Pepsin" refers to commercially available pepsin digest.

VITAMINS AND AMINO ACIDS

| Vitamins & Amino Acids | Method |
|---|---|
| L-Phenylaline | Extraction |
| Vitamin C | Extraction |
| Vitamin E | Extraction |
| Vitamin ED | Extraction |
| Inositol | Trace Mineral |
| Selenium Methionine | Trace Mineral |
| Soya Isolate | Trace Mineral |
| Trace Mineral Clay | Trace Mineral |
| Lysine | Compound |
| Pepsin | Compound |
| Whey Protein | Compound |
| Zinc Amino Acid Chelate | Compound |
| Co-enzyme Q | |
| Superoxide Dismutase | |
| Vegetable enzymes | |
| Iron Gluconate | |
| Copper amino acid gluconate | |
| Calcium amino acid gluconate | |
| L-Threonine | |
| Chromium niacin | |
| Selenium methionine | |
| L-phenylanaline | |

The invention will now be described by way of example.

The product formulae below show the dosage, for the disorders treatable by the composition, the amounts of the components used and therapies which may be used in combination with the compositions. Typically capsules contain between 200 mg and 1 g of composition per capsule.

The formulations may be taken neat or diluted with, for example 50% volume/volume cordial, fruit juice or lemonade.

The dosages may be separated into, for example, 3 equal doses taken after breakfast, lunch and an evening meal.

Skin care, massage and sports injury remedies may be applied topically directly onto the area to be "treated".

The Aloe vera, honey products, vitamins/amino acids, Indian brandee and blackcurrant concentrate are all commercially available products.

The Aloe vera products, heat lotion and propolis creme may be obtained from Forever Living Products (UK) Ltd, Longbridge Manor, Longbridge, Warwick, Warwickshire, United Kingdom. Aloe vera "juice" comprises as main ingredients stabilised Aloe vera gel, sorbitol, lemon juice, vitamin E, sodium benzoate and papain. "Pure" Aloe vera comprises stabilised Aloe vera gel, sorbitol, citric acid, vitamin E, sodium benzoate and papain. Aloe vera "nectar" comprises raw Alow vera gel, fructose, sorbitol, cranberry and apple juice concentrate, ascorbic acid, citric acid, potassium sorbate, sodium benzoate, xanthan gum, tocopherol and colourings.

Heat lotion comprises stabilized Aloe vera gel, DI water, propylene glycol, stearic acid, glyceryl stearate, triethanolamine, eucalyptus oil, methyl salicylate, apricot kernel oil, sesame oil, cetyl alcohol, petrolatum, lanolin, jojaba oil, oleic acid, stearyl stearate, dioctyl adipate, octyl stearate, octyl palmitate, PEG-100 stearate, allantoin, mineral oil, lanolin alcohol, ascorbic acid, diazolidinyl urea, methylparaben and propylparaben.

Propolis creme comprises stabilized Aloe vera gel, glyceryl stearate (and) PEG-1-00 stearate, propylene glycol, cetyl alcohol, dioctyl adipate (and) octyl stearate (and) octyl palmitate, lanolin, sorbitol, allantoin, bee propolis extract, lanolin alcohol, dimethicone, mineral oil, imodazolidinyl, urea, vitamins A & E, comfrey extract, chamomile extract, triethanolamine, ascorbic acid, methylparaben, propylparaben, fragrance.

Rescue remedy is a composition of five Bach flower remedies: Impatiens, Star of Bethlehem, Cherry Plum, Rock Rose and Clematis.

Except where indicated, the essential oils, Chinese herbs/Indian spices, honey products, vitamins/amino acids, Indian brandee and blackcurrant concentrate are mixed together in the amounts indicated with sufficient Aloe vera to make the final formulation up a final volume of 1,000 ml.

All components are from commercial sources. Vegetable enzymes are obtained as a commercially available product from "G and G Foods (UK)".

Initial results indicate that the specific essential oil and herb/spice combination of the invention provides effective compositions for medical and/or cosmetic use.

Patient Pilot Study

From a database of 250 people, having been diagnosed by their own practitioner as having M.E./Chronic Fatigue Syndrome, 80 responded to the inventors for information requesting to take the particular formula.

The findings of this initial pilot study indicated:

i) One third of the respondents diagnosed with M.E./Chronic Fatigue Syndrome did not have this condition. Most had Candida, depression or arthritis. A number suffered from a combination. Due to the similarity and overlap of many symptoms, without practitioners being able to measure the response by administering separate formula for each of these conditions, it is not possible for them to accurately disseminate between these four conditions.

ii) When a patient has been accurately diagnosed and they take the respective formula, as shown in Table 5, correctly, a full recovery is apparent at the end of the 25 day ingestion period.

iii) A pattern also became evident with about one third of patients making a partial recovery and in a few cases no realistic recovery. In all these cases it became apparent each respective formula of the inventors was being frustrated. After further discussion and analysis of the patient records a clear pattern emerged.

In the majority of cases these patients had been exposed to either one or a combination of the following traditional treatments:

Side Effects

|  | Side Effects |
|---|---|
| (a) X-rays/scans | Medical irradiation |
| (b) Medical drugs | Misfunction |
| (c) Amaigam dental fillings | Mercury poisoning |
| (d) Organophosphate exposure | Nervous system | iv) The inventors then developed an additional 'body cleanser/irrigator' formula (Table 6). After taking this 25 day formula the original formula still resting within these patients was then released to perform.

v) Due to the alarming number of patients from referrals and potential patients suffering from the side effects of the above traditional treatments, the Foundation has successfully combined the 'irrigator' within each of its main formula. This prevents patients from having to take two formulae which doubles both the cost and time.

TABLE 5

| Essential Oils | | Herbs/Spices |
|---|---|---|
| Bergamot | ¼ ml | Herbs: 5:1 |
| Camphor | ¼ ml | |
| Chamomile Roman | ¼ ml | Bai Guo Ya - 2 gm |
| Eucalyptus Globulus | ¼ ml | Ba Ji Tian - 2 gm |
| Ginger | ¼ ml | Chen Ziang - 2 gm |
| Juniper | ¼ ml | Dan Huang - 2 gm |
| Melissa | ¼ ml | Niu Bang Zi - 2 gm |
| Peppermint | ¼ ml | Salix Alba - 2 gm |
| Rose Geranium | ¼ ml | Zhi Zi - 2 gm |
| Rosemary | ¼ ml | |
| | | Spices: |
| Tea Tree | ¼ ml | Cinnamon Sugar - 10 gm |
| | | Cloves 10 gm |
| | | Coriander - 10 gm |
| | | Garlic - 10 g |
| | | Juniper Berries - 10 gm |

| Base ingredients | | Flavouring |
|---|---|---|
| | Aloe Vera/Amino Acids/ | Honey - 20 ml |
| Honey Products | Vitamins | Indian Brandee - |
| Royal Jelly - 20 gm | Aloe Vera: | 20 ml |
| Bee Propolis - 20 gm | 2/3 litre | Vanilla - 50 gm |
| Enzymes/Minerals | Amino Acids: | |
| Enzymes: | Copper Amino Acid | |
| Vegetable Enzymes - | Chelate - 30 gm | |
| 30 gm | Lythium Threonine - 30 gm | |

TABLE 5-continued

| Minerals: | Superoxide Dismutase |
|---|---|
| Calcium - 10 gm | (S.O.D.) - 30 gm |
| Garlic - 20 gm | Zinc Amino Acid Chelate - |
| Inositol - 25 gm | 5 gm |
| Iron - 10 gm | Vitamins: |
| Mineral Clay | VIT C - 30 gm |
| Powders - 30 gm | VIT E D - Alpha Tocapherol - |
| | 10 gm |

TABLE 6

| Aloe Vera Nectar | Essential Oils | | Chinese Herbs/Indian Spices |
|---|---|---|---|
| | Bergamol | 1 ml | Chinese Herbs: |
| | Chamomile German | 1 ml | Acacia Catechu - 30 gm |
| | Chamomile Maroc | 1 ml | Acanthopanax Gracilistylus - |
| | Chamomile Roman | 1 ml | 30 gm |
| | Cinnamon Zeylanicum | 1 ml | Caesalpinia Sappan - 30 gm |
| | Clove Buds | 1 ml | Epimedium Spinosa - 30 gm |
| | Eucalyptus Globulus | 1 ml | |
| | Frankincense | 1 ml | Indian Spices: |
| | Fennel | 1 ml | Asapoetidia - 20 gm |
| | Hyssop | 1 ml | Coconut Cream Block - 20 gm |
| | Juniper | 1 ml | Coriander - 20gm |
| | Lemon Grass | 1 ml | Fenugreek - 20 gm |
| | Mountain Savoury | 1 ml | Horseradish Ribbled - 20 gm |
| | Niaoull | 1 ml | |
| | Red Thyme | 1 ml | |
| | Rosemary | 1 ml | |
| | Rose Geranium | 1 ml | |
| | Tagestes | 1 ml | |
| | Yiang Yiang | 1 ml | |
| Honey Products | Vitamins/ Amino Acids | Other | Therapies |
| Royal Jelly - 4000 gm | VIT C - 30 gm | Indian Brandee - 20 ml | Chinese Acupuncture - 2 sessions |
| Bee Propolis - 1 ml | VIT E D - Alpha Tocapherol - 30 gm | Blackcurrant Concentrate - 20 ml | |
| | Inositol - 2500 mg | | |
| | Pepsin - 30 gm | | |
| | Selenium Methionine - 30 gm | | |
| | Soya Isolate - 30 gm | | |
| | Trace Mineral Clay - 30 gm | | |
| | Whey Protein - 50 gm | | |
| | Zinc Amino Acid Chelate - 30 gm | | |

PRODUCT FORMULA BY AILMENT & ILLNESS
Product Formula A
2 capsules 3 times daily over 20 days
*+Formula Z - CRA - 2 sessions with Aromatherapist/Reflexologist (minimum 2 hours apart, maximum 7 days apart)

| Angina | Atherosclerosis | Diabetes | Heartburn | Tumour |
| Artery Walls | Blood Pressure | Emphysema | Raynard's Disease | |
| Asthma | Cholesterol | *Meningitis | *Strokes & Heart Attacks | |

| Essential Oils | | Herbs/Spices | Base Ingredients | | Flavouring |
|---|---|---|---|---|---|
| Basil | ⅛ ml | Herbs: 5:1 | Honey Products | Aloe Vera/Amino Acids/Vitamins | Honey - 20 ml |
| Bergamot | ⅛ ml | Bai Guo Ye (Ginkgo) - 2 gm | Royal Jelly - 3:1 - 7 gm | Aloe Vera: | Indian Brandee - 20 ml |
| Camphor | ⅛ ml | Bu Gu Zhi - 2 gm | Bee Propolis - 4:1 - 5 gm | Over 70 nutrients - ¾ liter | Vanilla - 50 gm |
| Chamomile German | ⅛ ml | Ban Xia - 2 gm | Enzymes/Minerals | Amino Acids: | |
| Chamomile Maroc | ⅛ ml | Chen Xiang - 2 gm | Enzymes: | L-Threonine - 15 gm | |
| Chamomile Roman | ⅛ ml | Da Huang - 2 gm | Vegetable Enzymes - 15 gm | Vitamins: | |
| Cinnamon Leaf | ⅛ ml | Dang Shen - 2 gm | Minerals: | VIT C - 15 gm | |
| Clove Buds | ⅛ ml | Er Cha - 2 gm | Calcium Amino Acid Chelate 20% - 10 gm | VIT E D - Alpha Tocapherol - 10 gm | |
| Dill | ⅛ ml | Ge Gen - 2 gm | | | |
| Eucalyptus Globulus | ⅛ ml | Grapeseed - 15 mcg | Copper Amino Acid Chelate 20% - 15 gm | | |
| Fennel | ⅛ ml | Lu Jiao Shuang - 2 gm | | | |
| Frankincense | ⅛ ml | Ma Dou Ling - 10 gm (1:1) (Not UK) | Garlic - 5 gm | | |
| Hyssop | ⅛ ml | Mai Men Dong - 2 gm | Inositol 25 gm | | |
| Juniper | ⅛ ml | Mao Zhao Cao (Cats Claw) - 2 gm | Iron Gluconate 12.5% - 10 gm | | |
| Lavender | ⅛ ml | Niu Bang Zi - 2 gm | Mineral Clay Powders - 15 gm | | |
| Lemon Grass | ⅛ ml | Pycnogenol - 10 mcg | Superoxide Dismutase (S.O.D.) - 15 gm | | |
| Mountain Savoury | ⅛ ml | Salix Alba (White Willow) - 10 gm 1:1 | | | |
| Niaouli | ⅛ ml | Shen Jin Cao - 2 gm | Zinc Amino Acid Chelate 20% - 5 gm | | |
| Peppermint | ⅛ ml | Shu Di Huang - 2 gm | | | |
| Rose Geranium | ⅛ ml | Su Mu - 2 gm | | | |
| Rosemary | ⅛ ml | Suan Zao Ren - 2 gm | | | |
| Tagestes | ⅛ ml | Tian Nan Xing - 2 gm | | | |
| Thyme Red | ⅛ ml | Wu Jia Pi - 2 gm | | | |
| Ylang Ylang | ⅛ ml | Xing Ren - 2 gm | | | |
| | | Zhen Zhu Mu - 2 gm | | | |
| | | Zhi Mu - 2 gm | | | |
| | | Spices: | | | |
| | | Asafoetidia - 10 gm | | | |
| | | Cardamom - 10 gm | | | |
| | | Celery Salt - 10 gm | | | |
| | | Chilli Powder - 10 gm | | | |
| | | Coconut Cream Block - 10 gm | | | |
| | | Coriander - 10 gm | | | |
| | | Fenugreek - 10 gm | | | |
| | | Horseradish Ribbled - 10 gm | | | |
| | | Mace Ground - 10 gm | | | |
| | | Mixed Spices Sweet - 10 gm | | | |
| | | Nutmeg Powder - 10 gm | | | |

PRODUCT FORMULA BY AILMENT & ILLNESS
Product Formula B
2 capsules 3 times daily over 20 days
*+ Formula Z - CRB - 2 sessions with Aromatherapist/Reflexologist (minimum 2 hours apart, maximum 7 days apart)
**+ Formula Z - CRN - 2 sessions with Aromatherapist/Reflexologist (minimum 2 hours apart, maximum 7 days apart)

| | | | | |
|---|---|---|---|---|
| Abscess | **Candida (Thrush/Cystitis) | Endometrilis | Indigestion | *Organophosphate Disease (OP's) |
| Alcoholism | Colitis | **Hepatitis | *Irritable Bowel | Pre-Menstrual Syndrome |
| **Anorexia | Crohn's Disease | Hiatus Hernia | Menopause | Ulcers - External |
| **Bulimia | Diverticulitis | HRT | Menstrual Disorders | Ulcers - Internal |

| Essential Oils | | Herbs/Spices | Base Ingredients | | Flavouring |
|---|---|---|---|---|---|
| Bergamot | ⅛ ml | Herbs: 5:1 | Honey Products | Aloe Vera/Amino Acids/Vitamins | Honey - 20 ml |
| Black Pepper | ⅛ ml | Bai Guo Ye (Ginkgo) - 2 gm | Royal Jelly - 3:1 - 7 gm | Aloe Vera: | Indian Brandee - 20 ml |
| Camphor | ⅛ ml | Bai Zhu - 2 gm | Bee Propolis - 4:1 - 5 gm | Over 70 nutrients - ¾ liter | Vanilla - 50 gm |
| Chamomile German | ⅛ ml | Chai Hu - 2 gm | Enzymes/Minerals | Amino Acids: | |
| Chamomile Maroc | ⅛ ml | Da Huang - 2 gm | Enzymes: | Glutamine - 15 gm | |
| Chamomile Roman | ⅛ ml | Dang Gul - 2 gm (Dong Quai) | Vegetable Enzymes - 15 gm | L-Threonine - 15 gm | |
| Cinnamon Leaf | ⅛ ml | Dang Shen - 2 gm | Minerals: | Pycnogenol - 10 mcg | |
| Clove Buds | ⅛ ml | Er Cha - 2 gm | Calcium Amino Acid Chelate 20% - 10 gm | Superoxide Dismutase (S.O.D.) - 15 gm | |
| Eucalyptus Globulus | ⅛ ml | Grapeseed - 15 mcg | | Vitamins: | |
| Fennel | ⅛ ml | Gui Ban - 2 gm | Copper Amino Acid Chelate 20% - 15 gm | VIT C - 15 gm | |
| Frankincense | ⅛ ml | Jin Quian Cao - 2 gm | | VIT E D - Alpha Tocapherol - 10 gm | |
| Hyssop | ⅛ ml | Lu Jiao Shuang - 2 gm | Garlic - 5 gm | | |
| Juniper Berry | ⅛ ml | Mao Zhao Cao (Cats Claw) - 2 gm | Inositol 25 gm | | |
| Lemon Grass | ⅛ ml | Pycnogenol - 10 mcg | Iron Gluconate 12.5% - 10 gm | | |
| Mountain Savoury | ⅛ ml | Salix Alba (White Willow) - 10 gm 1:1 | Mineral Clay Powders - 15 gm | | |
| Niaouli | ⅛ ml | Shu Di Huang - 2 gm | Zinc Amino Acid Chelate 20% - 5 gm | | |
| Rose Geranium | ⅛ ml | Su Mu - 2 gm | | | |
| Rosemary | ⅛ ml | Wu Jia Pi - 2 gm | | | |
| Sweet Marjoram | ⅛ ml | Yan Hu Suo - 2 gm | | | |
| Tagestes | ⅛ ml | Zhi Zi - 2 gm | | | |
| Thyme Red | ⅛ ml | Spices: | | | |
| Ylang Ylang | ⅛ ml | Asafoetidia - 10 gm | | | |
| | | Cayenne Pepper - 10 gm | | | |
| | | Celery Salt - 10 gm | | | |
| | | Chilli Powder - 10 gm | | | |
| | | Coconut Cream Block - 10 gm | | | |
| | | Coriander - 10 gm | | | |
| | | Dill Seeds - 10 gm | | | |
| | | Fenugreek - 10 gm | | | |
| | | Ginger - 10 gm | | | |
| | | Horseradish Ribbled - 10 gm | | | |
| | | Mace Ground - 10 gm | | | |
| | | Mustard Seed Black - 10 gm | | | |
| | | Orris Root - 10 gm | | | |

PRODUCT FORMULA BY AILMENT & ILLNESS

Product Formula C1
(Prevention) - 2 capsules × 3 times daily for 20 days
***+ Formula Z - CRN - 2 sessions with Aromatherapist/Reflexologist (minimum 2 hours apart, maximum 7 days apart)

| Cold Antidote | | Coughs/Bronchitis | | Influenza Antidote | **Pneumonia | |
|---|---|---|---|---|---|---|
| Essential Oils | | Herbs/Spices | | Base Ingredients | | Flavouring |
| Bergamot | ⅛ ml | Herbs: 5:1 | | Honey Products | Aloe Vera/Amino Acids/Vitamins | Honey - 20 ml |
| Chamomile German | ⅛ ml | Da Huang - 2 gm | | Royal Jelly - 3:1 - 7 gm | Aloe Vera: | Indian Brandee - 20 ml |
| Chamomile Maroc | ⅛ ml | Echinacaea Angustifolia - 10 gm (1:1) | | Bee Propolis - 4:1 - 5 gm | Over 70 nutrients - ¾ liter | Vanilla - 50 gm |
| Chamomile Roman | ⅛ ml | Er Cha - 2 gm | | Enzymes/Minerals | Amino Acids: | |
| Cinnamon Leaf | ⅛ ml | Huang Lian - 2 gm | | Enzymes: | L- Threonine - 15 gm | |
| Clove Buds | ⅛ ml | Jin Yin Hua - 2 gm | | Vegetable Enzymes - 15 gm | Superoxide Dismutase (S.O.D.) - 15 gm | |
| Eucalyptus Globulus | ⅛ ml | Jie Geng - 2 gm | | Minerals: | Vitamins: | |
| Fennel | ⅛ ml | Lian ZI (Red) - 2 gm | | Calcium Amino Acid Chelate 20% - 10 gm | VIT C - 15 gm | |
| Frankincense | ⅛ ml | Long Yan Rou - 2 gm | | Copper Amino Acid Chelate 20% - 15 gm | VIT E D - Alpha Tocapherol - 10 gm | |
| Hyssop | ⅛ ml | Niu Bang Zi - 2 gm | | Garlic - 5 gm | | |
| Juniper | ⅛ ml | Sang Ye - 2 gm | | Inositol 25 gm | | |
| Lemon Grass | ⅛ ml | Su Mu - 2 gm | | Iron Gluconate 12.5% - 10 gm | | |
| Mountain Savoury | ⅛ ml | Wu Jia Pi - 2 gm | | Mineral Clay Powders - 15 gm | | |
| Myrtle Red | ⅛ ml | Xing Ren - 2 gm | | | | |
| Niaouli | ⅛ ml | Spices: | | | | |
| Patchouli | ⅛ ml | Asafoetidia - 10 gm | | Zinc Amino Acid Chelate 20% - 5 gm | | |
| Pine | ⅛ ml | Cassia - 10 gm | | | | |
| Rose Geranium | ⅛ ml | Chilli Powder - 10 gm | | | | |
| Rosemary | ⅛ ml | Coconut Cream Block - 10 gm | | | | |
| Spanish Marjoram | ⅛ ml | Coriander - 10 gm | | | | |
| Sweet Thyme | ⅛ ml | Cream of Tartar - 10 gm | | | | |
| Tagestes | ⅛ ml | Fenugreek - 10 gm | | | | |
| Thyme Red | ⅛ ml | Horseradish Ribbled - 10 gm | | | | |
| Ylang Ylang | ⅛ ml | Juniper Berries - 10 g | | | | |
| | | Mace Ground - 10 gm | | | | |
| | | Onion - 10 gm | | | | |

Product Formula C2
(Cure) - Phial (single 50 ml dose)
*+ Formula Z - CRC2 - 2 sessions with Aromatherapist/Reflexologist (minimum 2 hours apart, maximum 7 days apart)
***+ Formula Z - CRN - 2 sessions with Aromatherapist/Reflexologist (minimum 2 hours apart, maximum 7 days apart)

| Cold Antidote | Coughs/Bronchitis | *Influenza Antidote | **Pneumonia | |
|---|---|---|---|---|
| Essential Oils | Herbs/Spices | Base Ingredients | | Flavouring |

-continued

PRODUCT FORMULA BY AILMENT & ILLNESS

| | | Herbs: 5:1 | | Honey Products | Vitamins/Amino Acids | Honey - 20 ml |
|---|---|---|---|---|---|---|
| Camphor | ⅛ ml | | | | | |
| Chamomile Roman | ⅛ ml | Che Qian Cao - 2 gm | | Royal Jelly - 10 gm | VIT C - 15 gm | Indian Brandee - 20 ml |
| Eucalyptus Globulus | ⅛ ml | Dan Shen - 2 gm | | Bee Propolis - 10 gm | Inositol - 10 gm | Vanilla - 50 gm |
| Grand Fir | ⅛ ml | Echinacaea Angustifolia - 10 gm | | | Lysine (Amino Acid) - 10 gm | |
| Juniper | ⅛ ml | Huang Lian - 2 gm | | | | |
| Melissa | ⅛ ml | Jie Geng - 2 gm | | | | |
| Patchouli | ⅛ ml | Jin Yin Hua - 2 gm | | | | |
| Tagestes | ⅛ ml | Lian ZI (Red) - 2 gm | | | | |
| | | Long Yan Rou - 2 gm | | | | |
| | | Niu Bang Zi - 2 gm | | | | |
| | | Sang Ye - 2 gm | | | | |
| | | Xing Ren - 2 gm | | | | |
| | | Spices: | | | | |
| | | Allspice - 10 gm | | | | |
| | | Cinnamon Sugar - 10 gm | | | | |

PRODUCT FORMULA BY AILMENT & ILLNESS
Product Formula D
2 capsules 3 times daily over 20 days
*+ Followed by Formula F - Clarissa Balancing System
– 2 sessions with Aromatherapist/Reflexologist (minimum 2 hours apart, maximum 7 days apart)

| *Clinical Depression (inherited) Hypertension | | *Insomnia *Lifestyle Depression | | Mental Breakdown Post Natal Depression | | *Psychopathical Social Violence Stress | |
|---|---|---|---|---|---|---|---|
| Essential Oils | | Herbs/Spices | | Base Ingredients | | | Flavouring |
| Basil | ⅛ ml | Herbs: 5:1 | | Aloe Vera/Amino Acids/Vitamins | | | Honey - 20 ml |
| Bergamot | ⅛ ml | Bai Dou Kou - 2 gm | | Aloe Vera: | | | Indian Brandee - 20 ml |
| Chamomile German | ⅛ ml | Bai Guo Ye (Ginkgo) - 2 gm | | Over 70 nutrients - ¾ liter | | | Vanilla - 50 gm |
| Chamomile Maroc | ⅛ ml | Bai He - 2 gm | | Enzymes/Minerals | Amino Acids: | | |
| Chamomile Roman | ⅛ ml | Da Huang - 2 gm | | Enzymes: | L-Threonine - 15 gm | | |
| Cinnamon Leaf | ⅛ ml | Dang Shen - 2 gm | | Vegetable Enzymes - 15 gm | Phosphetidyl Cholim - 10 gm | | |
| Clove Buds | ⅛ ml | Du Zhong - 2 gm | | Minerals: | Superoxide Dismutase (S.O.D.) - 15 gm | | |
| Eucalyptus Globulus | ⅛ ml | Er Cha - 2 gm | | Calcium Amino Acid Chelate 20% - | Vitamins: | | |
| Fennel | ⅛ ml | Grapeseed - 15 mcg | | 10 gm | VIT C - 15 gm | | |
| Frankincense | ⅛ ml | Gui Ban - 2 gm | | Copper Amino Acid Chelate 20% - | VIT E D - Alpha Tocapherol - 10 gm | | |
| Grapefruit | ⅛ ml | Pycnogenol - 10 mcg | | 15 gm | | | |
| Hyssop | ⅛ ml | Su Mu - 2 gm | | Garlic - 5 gm | | | |
| Juniper | ⅛ ml | Tian Ma - 2 gm (Not UK) | | Inositol 25 gm | | | |
| Lemon Grass | ⅛ ml | Wu Jia Pi - 2 gm | | Iron Gluconate 12.5% - 10 gm | | | |
| Melissa | ⅛ ml | Yin Yang Huo - 2 gm | | Mineral Clay Powders - 15 gm | | | |
| Moutain Savoury | ⅛ ml | Spices | | Zinc Amino Acid Chelate 20% - | | | |
| Niaouli | ⅛ ml | Aniseed - 10 gm | | 5 gm | | | |
| Rose Geranium | ⅛ ml | Asafoetidia - 10 gm | | | | | |
| Rosemary | ⅛ ml | Chilli - 10 gm | | | | | |
| Sweet Marjoram | ⅛ ml | Coconut Cream Block - 10 gm | | | | | |
| Tagestes | ⅛ ml | Coconut Ground - 10 gm | | | | | |
| Thyme Red | ⅛ ml | Corlander - 10 gm | | | | | |
| Ylang Ylang | ⅛ ml | Fenugreek - 10 gm | | | | | |
| | | Horseradish Ribbled - 10 gm | | | | | |
| | | Mace Ground - 10 gm | | | | | |
| | | Mixed Spices Sweet - 10 gm | | | | | |

PRODUCT FORMULA BY AILMENT & ILLNESS
Product Formula E
2 capsules 3 times daily over 20 days

| Essential Oils | | Ear Ache, Throat Infections Eye Infections Herbs/Spices | Eye Retina Glaucoma | Gum Disorders Hay Fever | Mouth Infections Pharyngitis Base Ingredients | Sinusitis Flavouring |
|---|---|---|---|---|---|---|
| Aniseed | ⅛ ml | Herbs: 5:1 | | Honey Products | Aloe Vera/Amino Acids/Vitamins | Honey - 20 ml |
| Bergamot | ⅛ ml | Da Huang - 2 gm | | Royal Jelly - 3:1 - 7 gm | Aloe Vera: | Indian Brandee - 20 ml |
| Camphor | ⅛ ml | Er Cha - 2 gm | | Bee Propolis - 4:1 - 5 gm | Over 70 nutrients - ¾ liter | Vanilla 50 gm |
| Carrot | ⅛ ml | Grapeseed - 15 mcg | | Enzymes/Minerals | Amino Acids: | |
| Chamomile German | ⅛ ml | Jin Yin Hua - 2 gm | | Enzymes: | L-Threonine - 15 gm | |
| Chamomile Maroc | ⅛ ml | Pycnogenol - 10 mcg | | Vegetable Enzymes - 15 gm | Superoxide Dismutase (S.O.D.) - 15 gm | |
| Chamomile Roman | ⅛ ml | Qiang Huo - 2 gm | | Minerals: | Vitamins: | |
| Cinnamon Leaf | ⅛ ml | Salix Alba (White Willow) - 10 gm | | Calcium Amino Acid Chelate 20% - 10 gm | VIT C - 15 gm | |
| Clove Buds | ⅛ ml | 1:1 | | Copper Amino Acid Chelate 20% - 15 gm | VIT E D - Alpha Tocapherol - 10 gm | |
| Dill | ⅛ ml | Su Mu - 2 gm | | Garlic - 5 gm | | |
| Eccalyptus Globulus | ⅛ ml | Tian Nan Xing - 2 gm | | Garlic - 5 gm | | |
| Fennel | ⅛ ml | Wu Bei Zi - 2 gm | | Inositol 25 gm | | |
| Frankincense | ⅛ ml | Wu Jia Pi - 2 gm | | Iron Gluconate 12.5% - 10 gm | | |
| Hazel | ⅛ ml | Xing Ren - 2 gm | | Mineral Clay Powders - 15 gm | | |
| Hyssop | ⅛ ml | Yan Hu Suo - 2 gm | | Zinc Amino Acid Chelate 20% - | | |
| Juniper Berry | ⅛ ml | Zhi Zi - 2 gm | | | | |
| Lavender | ⅛ ml | Spices: | | | | |
| Lemon Grass | ⅛ ml | Arrowroot - 10 gm | | 5 gm | | |
| | | Asafoetidia - 10 gm | | | | |
| Mountain savoury | ⅛ ml | Chilli - 10 gm | | | | |
| Niaouli | ⅛ ml | Cloves - 10 gm | | | | |
| Peppermint | ⅛ ml | Coconut Cream Block - 10 gm | | | | |
| Rose Geranium | ⅛ ml | Coriander - 10 gm | | | | |
| Rosemary | ⅛ ml | Fennel - 10 gm | | | | |
| Sweet Marjoram | ⅛ ml | Fenugreek - 10 gm | | | | |
| Tagestes | ⅛ ml | Horseradish Ribbled - 10 gm | | | | |
| Thyme Red | ⅛ ml | Mace Ground - 10 gm | | | | |
| Thyme Sweet | ⅛ ml | Mixed Spices - Sweet - 10 gm | | | | |
| Ylang Ylang | ⅛ ml | Paprika - Sweet - 10 gm | | | | |

PRODUCT FORMULA BY AILMENT & ILLNESS

Product Formula F - CBA
2 sessions with Aromatherapist/Reflexologist (minimum 2 hours apart, maximum 7 days apart)
Clarissa Balancing System
Clarissa Carer Personal Balancing System
Lack of Self Confidence

| Flower Remedies | Essential Oils | | Herbs/Spices | Baase Ingredients | Carrier Oils |
|---|---|---|---|---|---|
| Agrimon - 1 ml | Bergamot | ⅛ ml | Herbs: 5:1 | Aloe Vera Pure - 20 ml | Avocado - 10 ml |
| Crab Apple - 1 ml | Chamomile Roman | ⅛ ml | Bai Dou Kou - 2 gm | Honey 20 ml | Grapeseed - 40 ml |
| Sweet Chestnut - | Eucalyptus Globulus | ⅛ ml | Da Huang - 2 gm | | Hazelnut - 10 ml |
| | Fennel | ⅛ ml | Ji Xue Teng - 2 gm | | |
| | Hyssop | ⅛ ml | Spices: | | |
| 1 ml | Juniper | ⅛ ml | Cassia Bark - 10 gm | | |
| | Niaoui | 18 ml | | | |

Product Formula F - CBB
2 sessions with Aroma therapist/Reflexologist (minimum 2 hours apart, maximum 7 days apart)
Clarissa Balancing System
Clarissa Carer Personal Balancing System
Love and Contentment

| Flower Remedies | Essential Oils | | Herbs/Spices | Base Ingredients | Carrier Oils |
|---|---|---|---|---|---|
| Aspen - 1 ml | Bergamot | ⅛ ml | Herbs: 5:1 | Aloe Vera Pure - 20 ml | Avocado - 10 ml |
| Chicory - 1 ml | Chamomile Roman | ⅛ ml | Da Huang - 2 gm | Honey - 20 ml | Grapeseed - 40 ml |
| Gorse- 1 ml | Eucalyptus Globulus | ⅛ ml | Gou Teng - 2 gm | | Hazelnut - 10 ml |
| Mimulus - | Fennel | ⅛ ml | Spices: | | |
| 1 ml | Hyssop | ⅛ ml | Allspice Ground - 10 gm | | |
| Vervain - 1 ml | Juniper | ⅛ ml | Dill Seeds - 10 gm | | |
| Wild Rose - 1 ml | Niaouli | ⅛ ml | | | |

PRODUCT FORMULA BY AILMENT & ILLNESS

Product Formula F - CBC
2 sessions with Aromatherapist/Reflexologist (minimum 2 hours apart, maximum 7 days apart)
Clarissa Balancing System
Clarissa Carer Personal Balancing System
Fear of Achievement

| Flower Remedies | Essential Oils | | Herbs/Spices | Base ingredients | Carrier Oils |
|---|---|---|---|---|---|
| Beech - 1 ml | Bergamot | ⅛ ml | Herbs: 5:1 | Aloe Vera Pure - 20 ml | Avocado - 10 ml |
| Clematis - 1 ml | Chamomile Roman | ⅛ ml | Da Huang - 2 gm | Honey - 20 ml | Grapeseed - 40 ml |
| Hornbeam - 1 ml | Eucalyptus Globulus | ⅛ ml | Jin Ying Zi - 2 gm | | Hazelnut - 10 ml |
| | Fennel | ⅛ ml | Sang Ye - 2 gm | | |
| | Hyssop | ⅛ ml | Spices: | | |
| Larch - 1 ml | Juniper | ⅛ ml | Asafoetidia - 10 gm | | |
| Mustard - 1 ml | Niaouli | ⅛ ml | Cloves Ground - 10 gm | | |
| Vine - 1 ml | | | | | |

PRODUCT FORMULA BY AILMENT & ILLNESS

Product Formula F - CBD  
2 sessions with Aromatherapist/Reflexologist (minimum 2 hours apart, maximum 7 days apart)  
Clarissa Balancing System  
Clarissa Carer Personal Balancing System  
Anger & Jealousy

| Flower Remedies | Essential Oils | | Herbs/Spices | Base ingredients | Carrier Oils |
| --- | --- | --- | --- | --- | --- |
| Centuary - | Bergamot | ⅛ ml | Herbs: 5:1 | Aloe Vera Pure - 20 ml | Avocado - 10 ml |
| 1 ml | Chamomile Roman | ⅛ ml | Da Huang - 2 gm | Honey - 20 ml | Grapeseed - 40 ml |
| Elm - 1 ml | Eucalyptus Globulus | ⅛ ml | Ye Ju Jua - 2 gm | | Hazelnut - 10 ml |
| Impatiens - | Fennel | ⅛ ml | Spices: | | |
| 1 ml | Hyssop | ⅛ ml | Cardamom Seeds - 10 gm | | |
| Walnut - 1 ml | Juniper | ⅛ ml | Fenugreek Powder - 10 gm | | |
| Wil Oat - 1 ml | Niaouli | ⅛ ml | | | |

PRODUCT FORMULA BY AILMENT & ILLNESS

Product Formula F - CBE  
2 sessions with Aromatherapist/Reflexologist (minimum 2 hours apart, maximum 7 days apart)  
Clarissa Balancing System  
Clarissa Carer Personal Balancing System  
Hate & Regret

| Flower Remedies | Essential Oils | | Herbs/Spices | Base Ingredients | Carrier Oils |
| --- | --- | --- | --- | --- | --- |
| Cerato - 1 ml | Bergamot | ⅛ ml | Herbs: 5:1 | Aloe Vera Pure - 20 ml | Avocado - 10 ml |
| Gentian - 1 ml | Chamomile Roman | ⅛ ml | Da Huang - 2 gm | Honey - 20 ml | Grapeseed - 40 ml |
| Heather - | Eucalyptus Globulus | ⅛ ml | Fu Pen Zi - 2 gm | | Hazelnut - 10 ml |
| | Fennel | ⅛ ml | Spices: | | |
| 1 ml | Hyssop | ⅛ ml | Caraway Ground - 10 gm | | |
| Oak - 1 ml | Juniper | ⅛ ml | Chilli Powder - 10 gm | | |
| Rock Water - 1 ml | Niaouli | ⅛ ml | | | |
| Scleranthus - 1 ml | | | | | |

Product Formula F - CBF  
2 sessions with Aromatherapist/Reflexologist (minimum 2 hours apart, maximum 7 days apart)  
Clarissa Balancing System  
Clarissa Carer Personal Balancing System  
Lack of Self Esteem

| Flower Remedies | Essential Oils | | Herbs/Spices | Base Ingredients | Carrier Oils |
| --- | --- | --- | --- | --- | --- |
| Cherry Plum - 1 ml | Bergamot | ⅛ ml | Herbs: 5:1 | Aloe Vera Pure - 20 ml | Avocado - 10 ml |
| Holly - 1 ml | Chamomile Roman | ⅛ ml | Che Quian Cao - 2 gm | Honey 20 ml | Grapeseed - 40 ml |
| Olive - 1 ml | Eucalyptus Globulus | ⅛ ml | Da Huang - 2 gm | | Hazelnut - 10 ml |
| Red | Fennel | ⅛ ml | Su Mu - 2 gm | | |
| | Hyssop | ⅛ ml | Spices: | | |
| Chestnut - 1 ml | Juniper | ⅛ ml | Arrowroot Ground - 10 gm | | |
| Rock Rose - 1 ml | Niaouli | ⅛ ml | Cinnamon Ground - 10 gm | | |
| White Chestnut - 1 ml | | | | | |

PRODUCT FORMULA BY AILMENT & ILLNESS

Product Formula F - CBG
2 sessions with Aromatherapist/Reflexologist (minimum 2 hours apart, maximum 7 days apart)
Clarissa Balancing System
Clarissa Carer Personal Balancing System
Mental Strength & Stamina

| Flower Remedies | Essential Oils | | Herbs/Spices | Base Ingredients | Carrier Oils |
|---|---|---|---|---|---|
| Chestnut Bud - 1 ml | Bergamot | ⅛ ml | Herbs: 5:1 | Aloe Vera Pure - 20 ml | Avocado - 10 ml |
| Honeysuckle - 1 ml | Chamomile Roman | ⅛ ml | Da Huang - 2 gm | Honey - 20 ml | Grapeseed - 40 ml |
| Pine - 1 ml | Eucalyptus Globulus | ⅛ ml | Gou Teng - 2 gm | | Hazelnut - 10 ml |
| | Fennel | ⅛ ml | Hu Huang Lian - 10 gm | | |
| | Hyssop | ⅛ ml | Spices: | | |
| Star of Bethlehem - 1 ml | Juniper | ⅛ ml | Coriander Ground - 10 gm | | |
| Water Violet - 1 ml | Niaouli | ⅛ ml | Laos Powder - 10 gm | | |
| Willow - 1 ml | | | | | |
| Rescue Remedy - 1 ml | | | | | |

Product Formula F - CBH
2 sessions with Aromatherapist/Reflexologist (minimum 2 hours apart, maximum 7 days apart)
Clarissa Balancing System
Clarissa Carer Personal Balancing System
Guilt & Responsibility

| Flower Remedies | Essential Oils | | Herbs/Spices | Base Ingredients | Carrier Oils |
|---|---|---|---|---|---|
| Aspen - 1 ml | Bergamot | ⅛ ml | Herbs: 5:1 | Aloe Vera Pure - 20 ml | Avocado - 10 ml |
| Cherry Plum - 1 ml | Chamomile Roman | ⅛ ml | Bai Guo - 2 gm | Honey - 20 ml | Grapeseed - 40 ml |
| Elm - 1 ml | Eucalyptus Globulus | ⅛ ml | Da Huang - 2 gm | | Hazelnut - 10 ml |
| Honeysuckle - 1 ml | Fennel | ⅛ ml | Hu Po - 2 gm | | |
| | Hyssop | ⅛ ml | Spices: | | |
| | Juniper | ⅛ ml | Cardamom - 10 gm | | |
| | Niaouli | ⅛ ml | Fennel Powder - 10 gm | | |

PRODUCT FORMULA BY AILMENT & ILLNESS

Product Formula F - CBT
2 sessions with Aromatherapist/Reflexologist (minimum 2 hours apart, maximum 7 days apart)
Clarissa Balancing System
Clarissa Carer Personal Balancing System
Abuse, Trauma & Shock

| Flower Remedies | Essential Oils | | Herbs/Spices | Base Ingredients | Carrier Oils |
|---|---|---|---|---|---|
| Chicory - 1 ml | Bergamot | ⅛ ml | Herbs: 5:1 | Aloe Vera Pure - 20 ml | Avocado - 10 ml |
| Gorse - 1 ml | Chamomile Roman | ⅛ ml | Chan Tui - 2 gm | Honey - 20 ml | Grapeseed - 40 ml |
| Rescue Remedy - 1 ml | Eucalyptus Globulus | ⅛ ml | Da Huang - 2 gm | | Hazelnut - 10 ml |
| | Fennel | ⅛ ml | Jin Ying Zi - 2 gm | | |
| | Hyssop | ⅛ ml | Spices: | | |
| | Juniper | ⅛ ml | Carob - 10 gm | | |
| | Niaouli | ⅛ ml | Dill - 10 gm | | |

-continued

PRODUCT FORMULA BY AILMENT & ILLNESS

Product Formula F - CBV
2 sessions with Aromatherapist/Reflexologist (minimum 2 hours apart, maximum 7 days apart)
Clarissa Balancing System
Bereavement/Loss

| Flower Remedies | Essential Oils | | Herbs/Spices | Base Ingredients | Carrier Oils |
|---|---|---|---|---|---|
| Centaury - 1 ml | Bergamot | ⅛ ml | Herbs: 5:1 | Aloe Vera Pure - 20 ml | Avocado - 10 ml |
| Chicory - 1 ml | Chamomile Roman | ⅛ ml | Ba Ji Tian - 2 gm | Honey - 20 ml | Grapeseed - 40 ml |
| Hornbeam - 1 ml | Eucalyptus Globulus | ⅛ ml | Da Huang - 2 gm | | Hazelnut - 10 ml |
| Rock Water - 1 ml | Fennel | ⅛ ml | Xian He Cao - 2 gm | | |
| | Hyssop | ⅛ ml | Spices: | | |
| | Juniper | ⅛ ml | Anise Star - 10 gm | | |
| | Niaouli | ⅛ ml | Chilli - 10 gm | | |

PRODUCT FORMULA BY AILMENT & ILLNESS
Product Formula G
Phial (Single 50 ml dose)
Gastroenteritis
Sickness

| Essential Oils | | Herbs/Spices | Vitamins/Amino Acids | Flavouring |
|---|---|---|---|---|
| Chamomile Maroc | ⅛ ml | Herbs: 5:1 | VIT C - 15 gm | Vanilla - 50 gm |
| Hyssop | ⅛ ml | Bai Jiang Cao - 2 gm | Inositol - 25 gm | Honey - 10 ml |
| Lavender | ⅛ ml | Bai Zhu - 2 gm | Vegetable Enzymes - 15 gm | Indian Brandee - 10 ml |
| Niaouli | ⅛ ml | Da Huang - 2 gm | | |
| | | Shen Jin Cao - 2 gm | | |
| | | Spices: | | |
| | | Carbo - 10 gm | | |
| | | Coconut Powder - 10 gm | | |
| | | Fenugreek - 10 gm | | |

PRODUCT FORMULA BY AILMENT & ILLNESS
Product Formula H
Phial (Single 50 ml dose)
Headache
Migraine

| Essential Oils | | Herbs/Spices | Vitamins/Amino Acids | Flavouring |
|---|---|---|---|---|
| Basil | ⅛ ml | Herbs: 5:1 | VIT C - 15 gm | |
| Bergamot | ⅛ ml | Da Huang - 2 gm | Inositol - 25 gm | |
| Camphor | ⅛ ml | Salix Alba (White Willow) - 10 gm 1:1 | Vegetable Enzymes - 15 gm | |
| Chamomile Roman | ⅛ ml | Su Mu - 2 gm | | |
| Dill | ⅛ ml | Yan Hu Suo - 2 gm | | |
| Eucalyptus Globulus | ⅛ ml | Yang Rong Wan - 2 gm (Patent) | | |
| Fennel | ⅛ ml | Spices: | | |
| Ginger | ⅛ ml | | | |
| Hyssop | ⅛ ml | Caraway Gound - 10 gm | | |
| Juniper | ⅛ ml | Fennel - 10 gm | | |
| Niaouli | ⅛ ml | | | |
| Patchouli | ⅛ ml | | | |

PRODUCT FORMULA BY AILMENT & ILLNESS
Product Formula I
- 2 capsules 3 times daily over 20 days
Infertility

| Essential Oils | | Herbs/Spices | | Base Ingredients | | Flavouring | |
| --- | --- | --- | --- | --- | --- | --- | --- |
| Basil | ⅛ ml | Herbs: 5:1 | | Honey Products | | Aloe Vera/Amino Acids/Vitamins | Honey - 20 ml |
| Bergamot | ⅛ ml | Da Huang - 2 gm | | Royal Jelly - 3:1 - 7 gm | | Aloe Vera: | Indian Brandee - 20 ml |
| Chamomile German | ⅛ ml | Er Cha - 2 gm | | Bee Propolis - 4:1 - 5 gm | | Over 70 nutrients - ¾ liter | Vanilla - 50 gm |
| Chamomile Maroc | ⅛ ml | Huai Jiao Zi - 2 gm | | Enzymes/Minerals | | Amino Acids: | |
| Chamomile Roman | ⅛ ml | Lian Zi (Red) - 2 gm | | Enzymes: | | L-Threonine - 15 gm | |
| Cinnamon Leaf | ⅛ ml | Lu Jiao Shuang - 2 gm | | Vegetable Enzymes - 15 gm | | Superoxide Dismutase (S.O.D.) - 15 gm | |
| Clove Buds | ⅛ ml | Su Mu - 2 gm | | Minerals: | | Vitamins: | |
| Eucalyptus Globulus | ⅛ ml | Wu Jia Pi - 2 gm | | Calcium Amino Acid Chelate 20% - 10 gm | | VIT C - 15 gm | |
| Fatigue | ⅛ ml | Spices: | | Copper Amino Acid Chelate 20% - 15 gm | | VIT E D - Alpha Tocapherol - 10 gm | |
| Fennel | ⅛ ml | Asafoetidia - 10 gm | | Garlic - 5 gm | | | |
| Frankincense | ⅛ ml | Carob - 10 gm | | Inositol 25 gm | | | |
| Hyssop | ⅛ ml | Chilli Powder - 10 gm | | Iron Gluconate 12.5% - 10 gm | | | |
| Juniper | ⅛ ml | Cinnamon Sugar - 10 gm | | Mineral Clay Powders - 15 gm | | | |
| Lavender | ⅛ ml | Coconut Cream Block - 10 gm | | Zinc Amino Acid Chelate 20% - 5 gm | | | |
| Lemon Grass | ⅛ ml | Coriander - 10 gm | | | | | |
| Mountain Savoury | ⅛ ml | Fenugreek - 10 gm | | | | | |
| Niaouli | ⅛ ml | Ginger - 10 gm | | | | | |
| Patchouli | ⅛ ml | Horseradish Ribbled - 10 gm | | | | | |
| Rose Geranium | ⅛ ml | Juniper Berries -10 gm | | | | | |
| Rosemary | ⅛ ml | Mace Ground - 10 gm | | | | | |
| Tagestes | ⅛ ml | | | | | | |
| Thyme Red | ⅛ ml | | | | | | |
| Ylang Ylang | ⅛ ml | | | | | | |

PRODUCT FORMULA BY AILMENT & ILLNESS
Product Formula J
2 capsules 3 times daily over 20 days
*+Formula Z - CRJ - 2 sessions with Aromatherapist/Reflexologist (minimum 2 hours apart, maximum 7 days apart)
**+Formula Z - CRN - 2 sessions with Aromatherapist/Reflexologist (minimum 2 hours apart, maximum 7 days apart)

| | | | | | |
| --- | --- | --- | --- | --- | --- |
| **Acne | Athletes Foot | Dermatitis | *Herpes | **Leukaemia | |
| **Aids | *Batten'Disease | Eczema | Kidney Performance | *Parkinson's Disease | *Senile Dementia |
| *Alzheimers Disease | **Cancer | Hair & Scalp Conditions | Labyrinthitis | Psoriasis | Shingles |

| Essential Oils | | Herbs/Spices | | Base Ingredients | | Flavouring | |
| --- | --- | --- | --- | --- | --- | --- | --- |
| Bergamot | ⅛ ml | Herbs: 5:1 | | Honey Products | | Aloe Vera/Amino Acids/Vitamins | Honey - 20 ml |
| Camphor | ⅛ ml | Bai Guo Ye (Ginkgo) - 2 gm | | Royal Jelly - 3:1 - 7 gm | | Aloe Vera: | Indian Brandee - 20 ml |
| Chamomile German | ⅛ ml | Ba Ji Tian - 2 gm | | Bee Propolis - 4:1 - 5 gm | | Over 70 nutrients - ¾ liter | Vanilla - 50 gm |
| Chamomile Maroc | ⅛ ml | Da Huang - 2 gm | | Enzymes/Minerals | | Amino Acids: | |
| Chamomile Roman | ⅛ ml | Dang Shen - 2 gm | | Enzymes: | | Copper Amino Acid Chelate - 15 gm | |
| Cinnamon Leaf | ⅛ ml | Er Cha - 2 gm | | Vegetable Enzymes - 15 gm | | Glutamine - 15 gm | |
| Clove Buds | ⅛ ml | Grapeseed - 15 mcg | | Minerals: | | L-Threonine - 15 gm | |
| Eucalyptus Globulus | ⅛ ml | Pycnogenol - 10 mcg | | Calcium Amino Acid Chelate 20% - 10 gm | | Superoxide Dismutase (S.O.D.) - 15 gm | |
| Fennel | ⅛ ml | Salix Alba (White Willow) - 10 gm 1:1 | | Copper Amino Acid Chelate 20% - 15 gm | | Vitamins: | |
| Frankincense | ⅛ ml | Shu Di Huang - 2 gm | | Garlic - 5 gm | | VIT C - 15 gm | |
| Hyssop | ⅛ ml | Su Mu - 2 gm | | Inositol 25 gm | | VIT E D - Alpha Tocapherol - 10 gm | |
| Juniper | ⅛ ml | Wu Jia Pi - 2 gm | | Iron Gluconate 12.5% - 10 gm | | | |
| Lemon Grass | ⅛ ml | Wu Yao - 2 gm | | Mineral Clay Powders - 15 gm | | | |
| Mountain Savoury | ⅛ ml | Zhen Zhu Mu - 2 gm | | Zinc Amino Acid Chelate 20% - 5 gm | | | |
| Niaouli | ⅛ ml | Spices: | | | | | |
| Rosemary | ⅛ ml | Allspice - 10 gm | | | | | |
| Rose Geranium | ⅛ ml | Asafoetidia - 10 gm | | | | | |
| Tagestes | ⅛ ml | Cayenne Pepper - 10 gm | | | | | |
| Thyme Red | ⅛ ml | Chilli Powder - 10 gm | | | | | |
| Ylang Ylang | ⅛ ml | Coriander - 10 gm | | | | | |
| | | Dill Seeds - 10 gm | | | | | |
| | | Fenugreek - 10 gm | | | | | |
| | | Horseradish Ribbled - 10 gm | | | | | |
| | | Mace Ground - 10 gm | | | | | |
| | | Slippery Elm - 10 gm | | | | | |

PRODUCT FORMULA BY AILMENT & ILLNESS
Product Formula K
- 2 capsules 3 times daily over 20 days Cerebral Palsy  
Chicken Pox  
Epilepsy  
Measles  
Mumps  
Scarlet Fever

| Essential Oils | | Herbs/Spices | Base Ingredients | Flavouring |
|---|---|---|---|---|
| Basil | ⅛ ml | Herbs: 5:1 | Honey Products | Aloe Vera/Amino | Honey - 20 ml |
| Bergamot | ⅛ ml | Chi Shao Yao - 2 gm | Royal Jelly - 3:1 - 7 gm | Acids/Vitamins | Indian Brandee - 20 ml |
| Carrot | ⅛ ml | Da Huang - 2 gm | Bee Propolis - 4:1 - 5 gm | Aloe Vera: | Vanilla - 50 gm |
| Chamomile German | ⅛ ml | Er Cha - 2 gm | Enzymes/Minerals | Over 70 nutri- | |
| Chamomile Maroc | ⅛ ml | Guo Teng - 2 gm | Enzymes: | ents - ¾ liter | |
| Chamomile Roman | ⅛ ml | Huang Lian - 2 gm | Vegetable Enzymes - 15 gm | Amino Acids: | |
| Cinnamon Leaf | ⅛ ml | Mao Zhao Cao (Cats Claw) - 2 gm | Minerals: | L-Threonine - 15 gm | |
| Clove Buds | ⅛ ml | Mu Tong - 2 gm | Calcium Amino Acid Chelate 20% - 10 gm | Superoxide Dismutase (S.O.D.) - 15 gm | |
| Eucalyptus Globulus | ⅛ ml | Niu Bang Zi - 2 gm | Copper Amino Acid Chelate 20% - 15 gm | Vitamins: | |
| Fennel | ⅛ ml | Su Mu - 2 gm | Garlic - 5 gm | VIT C - 15 gm | |
| Frankincense | ⅛ ml | Wu Jia Pi - 2 gm | Inositol 25 gm | VIT E D - Alpha Tocapherol - 10 gm | |
| Hyssop | ⅛ ml | Spices: | Iron Gluconate 12.5% - 10 gm | | |
| Juniper | ⅛ ml | Asafoetidia - 10 gm | Mineral Clay Powders - 15 gm | | |
| Lemon Grass | ⅛ ml | Chilli Powder - 10 gm | Zinc Amino Acid Chelate 20% - 5 gm | | |
| Mountain Savoury | ⅛ ml | Coconut Cream Block - 10 gm | | | |
| Niaouli | ⅛ ml | Coconut Ground - 10 gm | | | |
| Rose Geranium | ⅛ ml | Coriander - 10 gm | | | |
| Rosemary | ⅛ ml | Dutch Caraway - 10 gm | | | |
| Tagestes | ⅛ ml | Fenugreek - 10 gm | | | |
| Thyme Red | ⅛ ml | Horseradish - 10 gm | | | |
| Ylang Ylang | ⅛ ml | Mace Ground - 10 gm | | | |
| | | Mixed Spices Sweet - 10 gm | | | |

PRODUCT FORMULA BY AILMENT & ILLNESS
Product Formula L
- 2 capsules 3 times daily over 20 days  
Birth Control

| Essential Oils | | Herbs/Spices | Base Ingredients | Flavouring |
|---|---|---|---|---|
| Aniseed | ⅛ ml | Herbs: 5:1 | Honey Products | Aloe Vera/Amino | Honey - 20 ml |
| Bergamot | ⅛ ml | Da Huang - 2 gm | Royal Jelly - 3:1 - 7 gm | Acids/Vitamins | Indian Brandee - 20 ml |
| Chamomile German | ⅛ ml | Er Cha - 2 gm | Bee Propolis - 4:1 - 5 gm | Aloe Vera: | Vanilla - 50 gm |
| Chamomile Maroc | ⅛ ml | He Zi - 2 gm | Enzymes/Minerals | Over 70 nutri- | |
| Chamomile Roman | ⅛ ml | Jin Ying Zi - 2 gm | Enzymes: | ents - ¾ liter | |
| Cinnamon Leaf | ⅛ ml | Mao Zhao Cao (Cats Claw) - 2 gm | Vegetable Enzymes - 15 gm | Amino Acids: | |
| Clove Buds | ⅛ ml | Mu Hu Die - 2 gm | Minerals: | L-Threonine - 15 gm | |
| Eucalyptus Globulus | ⅛ ml | Su Mu - 2 gm | Calcium Amino Acid Chelate 20% - 10 gm | Superoxide Dismutase (S.O.D.) - 15 gm | |
| Fennel | ⅛ ml | Wu Jia Pi - 2 gm | Copper Amino Acid Chelate 20% - 15 gm | Vitamins: | |
| Frankincense | ⅛ ml | Yam - 2 gm | Garlic - 5 gm | VIT C - 15 gm | |
| Hyssop | ⅛ ml | Spices: | Inositol 25 gm | VIT E D - Alpha Tocapherol - 10 gm | |
| Juniper | ⅛ ml | Asafoetidia - 10 gm | Iron Gluconate 12.5% - 10 gm | | |
| Lavender | ⅛ ml | Cardamom - 10 gm | Mineral Clay Powders - 15 gm | | |
| Lemon Grass | ⅛ ml | Chilli Powder - 10 gm | Zinc Amino Acid Chelate 20% - 5 gm | | |
| Mountain Savoury | ⅛ ml | Coconut Cream Block - 10 gm | | | |
| Niaouli | ⅛ ml | Coriander - 10 gm | | | |
| Rose Geranium | ⅛ ml | Fennel - 10 gm | | | |
| Rosemary | ⅛ ml | Fenugreek - 10 gm | | | |
| Tagestes | ⅛ ml | Horseradish Ribbled - 10 gm | | | |
| Thyme Red | ⅛ ml | Mace - 10 gm | | | |
| Ylang Ylang | ⅛ ml | Onion - 10 gm | | | |

PRODUCT FORMULA BY AILMENT & ILLNESS
Product Formula M
- 2 capsules 3 times daily over 20 days
*+Formula Z - CRM - 2 sessions with Aromatherapist/Reflexologist (minimum 2 hours apart, maximum 7 days apart)

| *Anaemia | *ME | *MS |
|---|---|---|
| Glandular Fever | *Motor Neurone Disease | *Muscular Dystrophy |
| Lypus | M.R.S.A. virus | *Thyroid Gland (over and under active) |

| Essential Oils | | Herbs/Spices | Base Ingredients | | Flavouring |
|---|---|---|---|---|---|
| Bergamot | ⅛ ml | Herbs: 5:1 | Honey Products | Aloe Vera/Amino | Honey - 20 ml |
| Camphor | ⅛ ml | Bai Guo Ye (Ginkgo) - 2 gm | Royal Jelly - 3:1 - 7 gm | Acids/Vitamins | Indian Brandee - 20 ml |
| Chamomile German | ⅛ ml | Ba Ji Tian - 2 gm | Bee Propolis - 4:1 - 15 gm | Aloe Vera: | Vanilla - 50 gm |
| Chamomile Maroc | ⅛ ml | Chen Xiang - 2 gm | Enzymes/Minerals | Over 70 nutri- | |
| Chamomile Roman | ⅛ ml | Da Huang - 2 gm | Enzymes: | ents- ¾ liter | |
| Cinnamon Leaf | ⅛ ml | Er Cha - 2 gm | Vegetable Enzymes - 15 gm | Amino Acids: | |
| Clove Buds | ⅛ ml | Grapeseed - 15 mcg | Minerals: | L-Threonine - 15 gm | |
| Eucalyptus Globulus | ⅛ ml | Huang Lian - 2 gm | Calcium Amino Acid Chelate 20% - | Superoxide Dismutase | |
| Fennel | ⅛ ml | Mao Zhao Cao (Cats Claw) - 2 gm | 10 gm | (S.O.D.) - 15 gm | |
| Frankincense | ⅛ ml | Niu Bang Zi - 2 gm | Copper Amino Acid Chelate 20% - | Vitamins: | |
| Ginger | ⅛ ml | Pycnogenol - 10 mcg | 15 gm | VIT C - 15 gm | |
| Hyssop | ⅛ ml | Salix Alba (White Willow) - 10 gm | Garlic - 5 gm | VIT E D - Alpha | |
| Juniper | ⅛ ml | 1:1 | Inositol 25 gm | Tocapherol - 10 gm | |
| Lemon Grass | ⅛ ml | Su Mu - 2 gm | Iron Gluconate 12.5% - 10 gm | | |
| Melissa | ⅛ ml | Wu Jia Pi - 2 gm | Mineral Clay Powders - 15 gm | | |
| Mountain Savoury | ⅛ ml | Zhi Zi - 2 gm | Zinc Amino Acid Chelate 20% - | | |
| Niaouli | ⅛ ml | Spices: | 5 gm | | |
| Peppermint | ⅛ ml | Asafoetidia- 10 gm | | | |
| Rose Geranium | ⅛ ml | Chilli Powder - 10 gm | | | |
| Rosemary | ⅛ ml | Cinnamon Sugar - 10 gm | | | |
| Tagestes | ⅛ ml | Cloves - 10 gm | | | |
| Tea Tree | ⅛ ml | Coconut Cream Block - 10 gm | | | |
| Thyme Red | ⅛ ml | Coriander - 10 gm | | | |
| Ylang Ylang | ⅛ ml | Fenugreek - 10 gm | | | |
| | ⅛ ml | Garlic - 10 g | | | |
| | ⅛ ml | Horseradish Ribbled - 10 gm | | | |
| | | Juniper Berries - 10 gm | | | |
| | | Mace Ground - 10 gm | | | |

PRODUCT FORMULA BY AILMENT & ILLNESS
*Product Formula N
NUTRITIONAL AND BODY CLEANSING DRINK SUPPLEMENT
- 10 ml daily preferably at bedtime - 90 days supply
Immune System

| Essential Oils | | Herbs/Spices | Base Ingredients | | Flavouring |
|---|---|---|---|---|---|
| Basil | ⅛ ml | Herbs: 5:1 | Honey Products | Aloe Vera: | Honey - 20 ml |
| Bergamot | ⅛ ml | Bai Guo Ye (Ginkgo) - 1 gm | Royal Jelly - 3:1 - 7 gm | Over 70 nutrients in- | Indian Brandee - 20 ml |
| Chamomile German | ⅛ ml | Bai Zhi - 1 gm | Bee Propolis -4:1 - 5 gm | cluding all vitamins | Vanilla 50 gm |
| Chamomile Maroc | ⅛ ml | Ban Xia - 1 gm | Enzymes: | B1–B16 - ¾ liter | |
| Chamomile Roman | ⅛ ml | Boswellia Serrata - 5 gm 1:1 | Co Enzyme Q10 - 10 mcg | Amino Acids: | |
| Cinnamon Leaf | ⅛ ml | Chai Hu - 1 gm | Vegetable Enzymes | Glucosamine | |
| Clove Buds | ⅛ ml | Da Huang - 1 gm | 4:1 - 7.5 gm | (n-Acetyl-d) - 7.5 gm | |
| Eucalyptus Globulus | ⅛ ml | Dang Gui (Dong Quai) - 1 gm | Minerals: | Glutamine - 15 gm | |
| Fennel | ⅛ ml | Dang Shen- 1 gm | Calcium Amino Acid Chelate | Hesperidin Complex - | |
| Frankincense | ⅛ ml | Er Cha - 1 gm | 20% - 5 gm | 7.5 gm | |
| Hyssop | ⅛ ml | Chamaelirium Lurea (False Unicorn) - | Chromium Niacin - 10 mcg | Histidine - 7.5 gm | |
| Juniper | ⅛ ml | 1 gm | Copper Amino Acid Chelate | Isoleucine - 7.5 gm | |
| Lemon Grass | ⅛ ml | Gou Qi Zi(Lychum) - 1 gm | 20% - 7.5 gm | L-Aspartic Acid - 7.5 gm | |
| Mountain Savoury | ⅛ ml | Grapeseed - 15 mcg | Devil's Claw - 7.5 gm | L-Phenylalenine - 7.5 gm | |
| Niaouli | ⅛ ml | Lu Jiao Shuang - 1 gm | Inositol - 12.5 gm | Lecithin - 7.5 gm | |
| Rose Geranium | ⅛ ml | Man Jing Zi - 1 gm | Iron Gluconate 12.5% - 5 gm | Lysine - 7.5 gm | |
| Rosemary | ⅛ ml | Mao Zhao Cao (Cats Claw) - 1 gm | Magnesium Amino Acid | L-Taurine - 7.5 gm | |
| Tagestes | ⅛ ml | Mexican Yam Root - 5 gm 1:1 | Chelate - 10 gm | L-Threonine - 7.5 gm | |
| Thyme Red | ⅛ ml | Pycnogenol - 10 mcg | Manganese Gluconate - 10 gm | Phosphatidyl Choline - | |
| Ylang Ylang | ⅛ ml | Rou Cong Rong - 1 gm | Mineral Clay Powders - 7.5 gm | 10 gm | |
| | | Salix Alba (White Willow) - 5 gm 1:1 | Molybdenum - 7.5 gm | Vitamins: | |
| | | Shan Zha-1 gm | Selenium Methionine 5% - 5 gm | Betacorotene Dunal- | |
| | | Sheng Ma - 1 gm | Superoxide Dismutase (S.O.D.) | lella Salina Algae | |

| PRODUCT FORMULA BY AILMENT & ILLNESS |||||
|---|---|---|---|---|
| *Product Formula N |||||
| NUTRITIONAL AND BODY CLEANSING DRINK SUPPLEMENT |||||
| - 10 ml daily preferably at bedtime - 90 days supply |||||
| Immune System |||||
| Essential Oils | Herbs/Spices | Base Ingredients | | Flavouring |
| | Su Mu - 1 gm | 7.5 gm | 2.5% - 7.5 gm | |
| | Wu Jia Pi - 1 gm | Zinc Amino Acid Chelate 20% - | Biotin - 5 mcg | |
| | Yi Mu Cao - 1 gm | 2.5 gm | Folic Acid - 15 gm | |
| | Yohimbe (prescription only) - 1 gm | Nutritional Oils & Fats | VIT C - 15 gm | |
| | Spices: | Cod Liver Powder- 7.5 gm | VIT E D - Alpha | |
| | Allspice - 5 gm | Evening Primrose - 15 ml | Tocapherol - 10 gm | |
| | Asafoetidia - 5 gm | Garlic Powder - 5 gm | K1 5% - 1 gm | |
| | Caraway Ground - 5 gm | Linoleic acid - 7.5 gm | | |
| | Chilli Powder - 5 gm | Linolenic acid - 7.5 gm | | |
| | Coconut Cream Block - 5 gm | Olive Oil - 15 ml | | |
| | Coriander - 5 gm | | | |
| | Cream of Tartar - 5 gm | | | |
| | Fenugreek - 5 gm | | | |
| | Horseradish Ribbled - 5 gm | | | |
| | Mace Ground - 5 gm | | | |

| PRODUCT FORMULA BY AILMENT & ILLNESS |||||
|---|---|---|---|---|
| Product Formula O |||||
| - 2 capsules 3 times daily over 20 days |||||
| Partial & Total Deafness |||||
| Essential Oils | Herbs/Spices | Base Ingredients | | Flavouring |
| Basil ⅛ ml | Herbs: 5:1 | Honey Products | Aloe Vera/Amino | Honey - 20 ml |
| Bergamot ⅛ ml | Bai Guo Ye (Ginkgo) - 2 gm | Royal Jelly - 3:1 - 7 gm | Acids/Vitamins | Indian Brandee - |
| Carrot ⅛ ml | Da Huang - 2 gm | Bee Propolis - 4:1 - 5 gm | Aloe Vera: | 20 ml |
| Chamomile German ⅛ ml | Er Cha - 2 gm | Enzymes/Minerals | Over 70 nutri- | Vanilla - 50 gm |
| Chamomile Maroc ⅛ ml | Gou Teng - 2 gm | Enzymes: | ents ¾ liter | |
| Chamomile roman ⅛ ml | Mu Li - 2 gm | Vegetable Enzymes - 15 gm | Amino Acids: | |
| Cinnamon Leaf ⅛ ml | Sang Ye - 2 gm | Minerals: | L-Threonine - 15 gm | |
| Clove Buds ⅛ ml | Su Mu- 2 gm | Calcium Amino Acid Chelate 20% - | Superoxide Dismutase | |
| Eucalyptus Globulus ⅛ ml | Wu Jia Pi - 2 gm | 10 gm | (S.O.D.) - 15 gm | |
| Fennel ⅛ ml | Ye Ju Hua - 2 gm | Copper Amino Acid Chelate 20% - | Vitamins: | |
| Frankincense ⅛ ml | Spices: | 15 gm | VIT C - 15 gm | |
| Hyssop ⅛ ml | Anise Star - 10 gm | Garlic - 5 gm | VIT E D - Alpha | |
| Juniper ⅛ ml | Asafoetidia - 10 gm | Inositol 25 gm | Tocapherol - 10 gm | |
| Lemon Grass ⅛ ml | Cassia - 10 gm | Iron Gluconate 12.5% - 10 gm | | |
| Melissa ⅛ ml | Chilli Powder - 10 gm | Mineral Clay Powders - 15 gm | | |
| Mountain Savoury ⅛ ml | Coconut Cream Block - 10 gm | Zinc Amino Acid Chelate 20% - | | |
| Niaouli ⅛ ml | Coriander - 10 gm | 5 gm | | |
| Rose Geranium ⅛ ml | Fennel - 10 gm | | | |
| Rosemary ⅛ ml | Fenugreek - 10 gm | | | |
| Tagestes ⅛ ml | Horseradish Ribbled - 10 gm | | | |
| Thyme Red ⅛ ml | Laos - 10 gm | | | |
| Ylang Ylang ⅛ ml | Mace Ground - 10 gm | | | |
| | Turmeric - 10 gm | | | |

PRODUCT FORMULA BY AILMENT & ILLNESS
Product Formula P
- 2 capsules 3 times daily over 20 days Impotence    Libido    Prostrate Gland

| Essential Oils | | Herbs/Spices | | Base Ingredients | Flavouring |
|---|---|---|---|---|---|
| Basil | ⅛ ml | Herbs: 5:1 | | Honey Products | Aloe Vera/Amino | Honey - 20 ml |
| Bergamot | ⅛ ml | Bai Guo Ye (Ginkgo) - 2 gm | | Royal Jelly - 3:1 - 7 gm | Acids/Vitamins | Indian Brandee - 20 ml |
| Chamomile German | ⅛ ml | Da Huang - 2 gm | | Bee Propolis - 4:1 - 5 gm | Aloe Vera: | Vanilla - 50 gm |
| Chamomile Maroc | ⅛ ml | Dang Gui (Dong Quai) - 2 gm | | Enzymes/Minerals | Over 70 nutri- | |
| Chamomile Roman | ⅛ ml | Er Cha - 2 gm | | Enzymes: | ents - ¾ liter | |
| Cinnamon Leaf | ⅛ ml | Grapeseed - 15 mcg | | Vegetable Enzymes - 15 gm | Amino Acids: | |
| Clove Buds | ⅛ ml | Huang Qi - 2 gm | | Minerals: | L-Threonine - 15 gm | |
| Eucalyptus Globulus | ⅛ ml | Jiang Can - 2 gm | | Calcium Amino Acid | Superoxide Dismut- | |
| Fatigue | ⅛ ml | Lian Zi (Red) - 2 gm | | Chelate 20% - 10 gm | ase (S.O.D.) - 15 gm | |
| Fennel | ⅛ ml | Lu Jiao Shuang - 2 gm | | Copper Amino Acid | Vitamins: | |
| Frankincense | ⅛ ml | Mai Ya - 2 gm | | Chelate 20% - 15 gm | VIT C - 15 gm | |
| Hyssop | ⅛ ml | Mu Dan Pi 2 gm | | Garlic - 5 gm | VIT E D - Alpha | |
| Juniper | ⅛ ml | Pycnogenol - 10 mcg | | Inositol 25 gm | Tocapherol - 10 gm | |
| Lavender | ⅛ ml | Shu Di Huang - 2 gm | | Iron Gluconate 12.5% - 10 gm | | |
| Lemon Grass | ⅛ ml | Su Mu - 2 gm | | Mineral Clay Powders - 15 gm | | |
| Mountain Savoury | ⅛ ml | Wu Jia Pi - 2 gm | | Zinc Amino Acid Chelate 20% - | | |
| Niaouli | ⅛ ml | Yohimbe (Prescrip- | | 5 gm | | |
| Rose Geranium | ⅛ ml | tion only) - 2 gm | | | | |
| Rosemary | ⅛ ml | Spices: | | | | |
| Tagestes | ⅛ ml | Allspice - 10 gm | | | | |
| Thyme Red | ⅛ ml | Asafoetidia - 10 gm | | | | |
| Ylang Ylang | ⅛ ml | Celery Salt - 10 gm | | | | |
| | ⅛ ml | Chilli Powder - 10 gm | | | | |
| | ⅛ ml | Coconut Cream Block - 10 gm | | | | |
| | | Coriander - 10 gm | | | | |
| | | Dill Seeds - 10 gm | | | | |
| | | Fenugreek- 10 gm | | | | |
| | | Garlic - 10 gm | | | | |
| | | Horseradish Ribbled - 10 gm | | | | |
| | | Mace Ground - 10 gm | | | | |

PRODUCT FORMULA BY AILMENT & ILLNESS
Product Formula Q
- 2 capsules 3 times daily over 20 days Abrasions, Bruises Burns, Cuts
Bunions

| Essential Oils | | Herbs/Spices | | Base Ingredients | Flavouring |
|---|---|---|---|---|---|
| Aniseed | ⅛ ml | Herbs: 5:1 | | Honey Products | Aloe Vera/Amino | Honey - 20 ml |
| Bergamot | ⅛ ml | Da Huang - 2 gm | | Royal Jelly - 3:1 - 7 gm | Acids/Vitamins | Indian Brandee - 20 ml |
| Camphor | ⅛ ml | Er Cha - 2 gm | | Bee Propolis - 4:1 - 5 gm | Aloe Vera: | Vanilla - 50 gm |
| Chamomile German | ⅛ ml | Jin Yin Hua - 2 gm | | Enzymes/Minerals | Over 70 nutri- | |
| Chamomile Maroc | ⅛ ml | Salix Alba (White Wil- | | Enzymes: | ents - ¾ liter | |
| Chamomile Roman | ⅛ ml | low) - 10 gm 1:1 | | Vegetable Enzymes - 15 gm | Amino Acids: | |
| Cinnamon Leaf | ⅛ ml | Su Mu - 2 gm | | Minerals: | L-Threonine - 15 gm | |
| Clove Buds | ⅛ ml | Wu Jia Pi - 2 gm | | Calcium Amino Acid | Superoxide Dismutase | |
| Eucalyptus Globulus | ⅛ ml | Spices: | | Chelate 20% - 10 gm | (S.O.D.) - 15 gm | |
| Fennel | ⅛ ml | Asafoetidia - 10 gm | | Copper Amino Acid | Vitamins: | |
| Frankincense | ⅛ ml | Chilli Powder - 10 gm | | Chelate 20% - 15 gm | VIT C - 15 gm | |
| Ginger | ⅛ ml | Cinnamon - 10 gm | | Garlic - 5 gm | VIT E D - Alpha | |
| Hyssop | ⅛ ml | Coconut Cream Block - 10 gm | | Inositol 25 gm | Tocapherol - 10 gm | |
| Juniper | ⅛ ml | Coriander - 10 gm | | Iron Gluconate 12.5% - 10 gm | | |
| Lemon Grass | ⅛ ml | Cream of Tartar - 10 gm | | Mineral Clay Powders - 15 gm | | |
| Mountain Savoury | ⅛ ml | Fennel - 10 gm | | Zinc Amino Acid Chelate 20% - | | |
| Niaouli | ⅛ ml | Fenugreek - 10 gm | | 5 gm | | |
| Rose Geranium | ⅛ ml | Horseradish Ribbled - 10 gm | | | | |
| Rosemary | ⅛ ml | Mace Ground - 10 gm | | | | |
| Tagestes | ⅛ ml | | | | | |
| Thyme Red | ⅛ ml | | | | | |
| Ylang Ylang | ⅛ ml | | | | | |

PRODUCT FORMULA BY AILMENT & ILLNESS
Product Formula R
2 capsules 3 times daily over 20 days
*+Formula Z - CRR - 2 sessions with Aromatherapist/Reflexologist
(minimum 2 hours apart, maximum 7 days apart)
Arthritis - Osteo
Arthritis - Rheumatoid
Gout
Inflammation, Back Ache, Sprains
*Osteoporosis
Scarcodosis
Sciatica
Varicose Veins

| Essential Oils | | Herbs/Spices | Base Ingredients | Flavouring |
|---|---|---|---|---|
| Bergamot | ⅛ml | Herbs: 5:1 | Honey Products | Aloe vera/Amino | Honey - 20 ml |
| Camphor | ⅛ml | Bai Guo Ye (Ginkgo) - 2 gm | Royal Jelly - 3:1 - 7 gm | Acids/Vitamins | Indian Brandee - |
| Chamomile German | ⅛ml | Bi Ji Tian - 2 gm | Bee Propolis - 4:1 - 5 gm | Aloe Vera: | 20 ml |
| Chamomile Maroc | ⅛ml | *Boswellia Serreta* - 1 gm | | Over 70 nutri- | Vanilla - 50 gm |
| Chamomile Roman | ⅛ml | Chen Xiang - 2 gm | Enzymes/Minerals | ents - ¾liter | |
| Cinnamon Leaf | ⅛ml | Da Huang - 2 gm | Enzymes: | Amino Acids: | |
| Clove Buds | ⅛ml | Dang Shen - 2 gm | Vegetable Enzymes - 15 gm | L-Threonine - 15 gm | |
| Eucalyptus Globulus | ⅛ml | Er Cha - 2 gm | | Superoxide Dismutase | |
| Fatigue | ⅛ml | Fu Ling - 2 gm | | (S.O.D.) - 15 gm | |
| Fennel | ⅛ml | Grapeseed - 15 mcg | Minerals: | Vitamins: | |
| Frankincense | ⅛ml | Jin Yin Hua - 2 gm | Calcium Amino Acid Chelate 20% - | VIT C - 15 gm. | |
| Ginger | ⅛ml | Mai Men Dong - 2 gm | 10 gm | VIT E D - Alpha | |
| Hyssop | ⅛ml | Mao Zhao Cao (Cats Claw) - 2 gm | Copper Amino Acid Chelate 20% - | Tocapherol - 10 gm | |
| Juniper | ⅛ml | Pycnogenol - 10 mcg | 15 gm | | |
| Lemon Grass | ⅛ml | Salix Alba (White Willow) - 10 gm | Garlic - 5 gm | | |
| Mountain Savoury | ⅛ml | 1:1 | Inositol 25 gm | | |
| Niaouli | ⅛ml | Su Mu - 2 gm | Iron Gluconate 12.5% - 10 gm | | |
| Red Myrtle | ⅛ml | Wu Jia Pi - 2 gm | Mineral Clay Powders - 15 gm | | |
| Rose Geranium | ⅛ml | Xian He Cao - 2 gm | Zinc Amino Acid Chelate 20% - | | |
| Rosemary | ⅛ml | Yan Hu Suo - 2 gm | 5 gm | | |
| Tagestes | ⅛ml | Zhi Mu - 2 gm | | | |
| Thyme Red | ⅛ml | Spices: | | | |
| Ylang Ylang | ⅛ml | Asafoetidia - 10 gm | | | |
| | | Cardamom - 10 gm | | | |
| | | Chilli Powder - 10 gm | | | |
| | | Coconut Cream Block - 10 gm | | | |
| | | Coriander - 10 gm | | | |
| | | Dutch Caraway - 10 gm | | | |
| | | Fenugreek - 10 gm | | | |
| | | Horseradish Ribbled - 10 gm | | | |
| | | Juniper Berries - 10 gm | | | |
| | | Laos Powder - 10 gm | | | |
| | | Mace Ground - 10 gm | | | |
| | | Turmeric - 10 gm | | | |

PRODUCT FORMULA BY AILMENT & ILLNESS
Product Formula S1
SPORTS PERFORMANCE & INJURIES
2 capsules 3 times daily over 20 days
**+Formula Z - CRN - 2 sessions with Aromatherapist/Reflexologist
(minimum 2 hours apart, maximum 7 days apart)
Internal Body Conditioner Stamina
**Energy Booster
Immune Balancing System

| Essential Oils | | Herbs and Spices | Base Ingredients | | Flavouring | Practitioners |
|---|---|---|---|---|---|---|
| Aniseed | ⅛ml | Herbs: 5:1 | Honey Products | Aloe Vera/Amino | Honey - 20 ml | Flower Remedy |
| Basil | ⅛ml | Bai Guo Ye (Ginkgo) - 2 gm | Royal Jelly - 3:1 - 7 gm | Acids/Vitamins | Indian Brandee - | Chinese |
| Bergamot | ⅛ml | Chi Shao Yao - 2 gm | Bee Propolis - 4:1 - 5 gm | Aloe Vera: | 20 ml | Acupuncture - |
| Chamomile German | ⅛ml | Da Huang - 2 gm | | Over 70 nutri- | Vanilla - 50 gm | 2 sessions |
| Chamomile Maroc | ⅛ml | Dang Gui (Dong Quai) - 2 gm | Enzymes/Minerals | ents - ¾liter | | Chiropractic - |
| Chamomile Roman | ⅛ml | Er Cha - 2 gm | Enzymes: | Amino Acids: | | 2 sessions |
| Cinnamon Leaf | ⅛ml | Fu Pen Zi - 2 gm | Vegetable Enzymes - | L-Threonine - 15 gm | | Alexander |
| Clove Buds | ⅛ml | Gou Teng - 2 gm | 15 gm | Superoxide | | Technique |

-continued

PRODUCT FORMULA BY AILMENT & ILLNESS
Product Formula S1
SPORTS PERFORMANCE & INJURIES
2 capsules 3 times daily over 20 days
**+Formula Z - CRN - 2 sessions with Aromatherapist/Reflexologist
(minimum 2 hours apart, maximum 7 days apart)
Internal Body Conditioner Stamina
**Energy Booster
Immune Balancing System

| Essential Oils | | Herbs and Spices | Base Ingredients | Flavouring | Practitioners |
|---|---|---|---|---|---|
| Eucalyptus Globulus | ⅛ml | Mao Zhao Cao (Cats Claw) - | Minerals: | Dismutase | |
| Fatigue | ⅛ml | 2 gm | Calcium Amino Acid | (S.O.D.) - 15 gm | |
| Fennel | ⅛ml | Mu Li - 2 gm | Chelate 20% - 10 gm | Vitamins: | |
| Frankincense | ⅛ml | Su Mu - 2 gm | Copper Amino Acid | VIT C - 15 gm | |
| Hyssop | ⅛ml | Wu Jia Pi - 2 gm | Chelate 20% - 15 gm | VIT E D - Alpha | |
| Juniper | ⅛ml | Spices: | Garlic - 5 gm | Tocapherol - 10 gm | |
| Lemon Grass | ⅛ml | Asafoetidia - 10 gm | Inositol 25 gm | | |
| Mountain Savoury | ⅛ml | Cassia - 10 gm | Iron Gluconate | | |
| Niaouli | ⅛ml | Chilli Powder - 10 gm | 1.25% - 10 gm | | |
| Rose Geranium | ⅛ml | Coconut Cream Block - | | | |
| Rosemary | ⅛ml | 10 gm | Mineral Clay | | |
| Tagestes | ⅛ml | Coriander - 10 gm | Powders - 15 gm | | |
| Thyme Red | ⅛ml | Dill Seeds- 10 gm | Zinc Amino Acid | | |
| Ylang Ylang | ⅛ml | Fenugreek - 10 gm | Chelate 20% - 5 gm | | |
| | ⅛ml | Horseradish Ribbled - 10 gm | | | |
| | ⅛ml | Juniper Berries - 10 gm | | | |
| | | Lemon Grass - 10 gm | | | |
| | | Mace Ground-10 gm | | | |
| | | Mixed Spices - 10 gm | | | |

PRODUCT FORMULA BY AILMENT & ILLNESS

| Aloe Vera | Essential Oils | Herbs/Spices | | Honey Products | Massage Oil | Practitioners |
|---|---|---|---|---|---|---|

Product Formula S2
EXTERNAL PHYSIO APPLICATION - SPORTS PERFORMANCE & INJURIES
Pre Performance Lotion (per 10 applications)

| Aloe Vera | Essential Oils | | Herbs/Spices | Honey Products | Massage Oil | Practitioners |
|---|---|---|---|---|---|---|
| Heat Lotion - | Aniseed | ⅛ml | Herbs: 5:1 | Bee Propolis - 4:1 - 5 gm | Avocado - 10 ml | |
| 20 gm | Basil | ⅛ml | Chi Shao Yao - 2 gm | | Grapeseed - 40 ml | |
| | Chamomile Maroc | ⅛ml | Qiang Huo - 2 gm | | Hazelnut - 10 ml | |
| | Fennel | ⅛ml | | | | |
| | | | Spices: | | | |
| | | | Cardamom - 10 gm | | | |
| | | | Ginger - 10 gm | | | |

Product Formula S3
EXTERNAL PHYSIO AND REFLEXOLOGY APPLICATION - SPORTS PERFORMANCE & INJURIES
+Formula Z - CRS3 - 2 sessions with Aromatherapist/Reflexologist
(minimum 2 hours apart, maximum 7 days apart)
Maintenance Recovery Massage (per 10 applications)

| Aloe Vera | Essential Oils | | Herbs/Spices | Honey Products | Massage Oil | Practitioners |
|---|---|---|---|---|---|---|
| Aloe | Aniseed | ⅛ml | Herbs: 5:1 | Bee Propolis - 4:1 - 5 gm | Avocado - 10 ml | Aromatherapy/ |
| Activator - | Basil | ⅛ml | Chi Shao Yao - 2 gm | | Grapeseed - 40 ml | Reflexology |
| 10 ml | Camphor | ⅛ml | Dang Gui (Dong Quai) - 2 gm | | Hazelnut - 10 ml | Application - |
| Heat Lotion - | Chamomile Maroc | ⅛ml | Salix Alba (White Willow) - 10 gm | | | 2 sessions |
| 20 gm | Eucalyptus Globulus | ⅛ml | 1:1 | | | |
| | Juniper | ⅛ml | Qiang Huo - 2 gm | | | |
| | | | Spices: | | | |
| | | | Asafoetidia - 10 gm | | | |
| | | | Fenugreek - 10 gm | | | |

| \multicolumn{6}{c}{PRODUCT FORMULA BY AILMENT & ILLNESS} |
| \multicolumn{6}{c}{EXTERNAL PHYSIO AND REFLEXOLOGY APPLICATION - SPORTS PERFORMANCE & INJURIES} |

| Aloe Vera | Essential Oils | Herbs/Spices | Honey Products | Massage Oil | Practitioners |
|---|---|---|---|---|---|
| | | Product Formula S4 | | | |
| | | Direct Internal & Surface Injury (per 10 applications) | | | |
| Aloe Activator - 10 ml Heat Lotion - 20 gm | Aniseed ⅛ml Basil ⅛ml Camphor ⅛ml Eucalyptus Globulus ⅛ml Fennel ⅛ml | Herbs: 5:1 Ba Ji Tian -2 gm Dang Gui (Dong Quai) - 2 gm Qiang Huo - 2 gm Salix Alba (White Willow) - 10 gm 1:1 Su Zi (Zi Su Zi) - 2 gm Spices: Ginger - 10 gm Horseradish - 10 gm | Bee Propolis - 4:1 - 5 gm | Avocado - 10 ml Grapeseed - 40 ml Hazelnut - 10 ml | Aromatherapy/ Reflexology Application - 2 sessions Osteopathy - 2 sessions |
| | | Product Formula S5 | | | |
| | | Cramp Fatigue Lotion (per 10 applications) | | | |
| Aloe Activator - 10 ml Heat Lotion - 20 gm | Camphor ⅛ml Rescue Remedy ⅛ml | Herbs: 5:1 Hu Po - 2 gm Huang Lian - 2 gm Salix Alba (White Willow) - 10 gm 1:1 Qiang Huo - 2 gm Spices: Chilli - 10 gm Lemon Grass - 10 gm | Bee Propolis - 4:1 - 5 gm | Avocado - 10 ml Grapeseed - 40 ml Hazelnut - 10 ml | Aromatherapy/ Reflexology Application - 2 sessions |

| \multicolumn{7}{c}{PRODUCT FORMULA BY AILMENT & ILLNESS} |
| \multicolumn{7}{c}{Product Formula S6} |
| \multicolumn{7}{c}{EXTERNAL PHYSIO AND REFLEXOLOGY APPLICATION - SPORTS PERFORMANCE & INJURIES} |
| \multicolumn{7}{c}{Fatigue Fractures (per 10 applications)} |

| Aloe Vera | Essential Oils | Herbs/Spices | Honey Products | Vitamins/ Amino Acids | Massage Oil | Practitioners |
|---|---|---|---|---|---|---|
| Aloe Activator - 10 ml Heat Lotion - 20 gm | Aniseed ⅛ml Basil ⅛ml Camphor ⅛ml Eucalyptus Globulus ⅛ml Ginger ⅛ml | Herbs: 5:1 Dang Gui (Dong Quai) - 2 gm Qiang Huo - 2 gm Salix Alba (White Willow) - 10 gm 1:1 Spices: Allspice - 10 gm Dill Seeds - 10 gm | Bee Propolis - 4:1 - 5 gm | B6 - 20 gm | Avocado - 10 ml Grapeseed - 40 ml Hazelnut - 10 ml | Aromatherapy/ Reflexology Application - 2 sessions |

PRODUCT FORMULA BY AILMENT & ILLNESS
Product Formula T
After crisis - 2 sessions with Aromatherapist/
Reflexologist (minimum 2 hours apart, maximum 7 days apart)
**Followed by Formula F - Clarissa Balancing System
- 2 sessions with Aromatherapist/Reflexologist
(minimum 2 hours apart, maximum 7 days apart)
Single 50 ml Dose
**Abuse (short term)
**Trauma/Shock (short term)

| Flower Remedies | Essential Oils | | Herbs/Indian Spices | Base Ingredients |
|---|---|---|---|---|
| Rescue Remedy - 1 ml | Dill | ⅛ml | Herbs: 5:1<br>Bu Gu Zhi - 2 gm<br>Chen Xiang - 2 gm<br>Guo Teng - 2 gm<br>Wu Be Zi - 2 gm<br>Spices:<br>Garlic - 10 gm<br>Laos - 10 gm | Aloe Vera Pure - 20 ml<br>Honey - 20 ml |

PRODUCT FORMULA BY AILMENT & ILLNESS
Product Formula U
- 2 capsules 3 times daily over 20 days
Schizophrenia

| Essential Oils | | Herbs/Spices | Base Ingredients | | Flavouring |
|---|---|---|---|---|---|
| Basil | ⅛ml | Herbs: 5:1 | Honey Products | Aloe Vera/Amino | Honey - 20 ml |
| Bergamot | ⅛ml | Da Huang - 2 gm | Royal Jelly - 3:1 - 7 gm | Acids/Vitamins | Indian Brandee - |
| Chamomile German | ⅛ml | Er Cha - 2 gm | Bee Propolis - 4:1 - 5 gm | Aloe Vera: | 20 ml |
| Chamomile Maroc | ⅛ml | Hu Huang Lian - 2 gm | | Over 70 nutrients - | Vanilla - 50 gm |
| Chamomile Roman | ⅛ml | Huo Ma Ren - 2 gm | Enzymes/Minerals | ¾liter | |
| Cinnamon Leaf | ⅛ml | Su Mu - 2 gm | Vegetable Enzymes - 15 gm | Amino Acids: | |
| Eucalyptus Globulus | ⅛ml | Ye Ju Hua - 2 gm | | L-Threonine - 15 gm | |
| Fennel | ⅛ml | | Minerals: | Superoxide Dismutase | |
| Frankincense | ⅛ml | Spices | Calcium Amino Acid Chelate 20% - | (S.O.D.) - 15 gm | |
| Ginger | ⅛ml | Allspice - 10 gm | 10 gm | Vitamins: | |
| Hyssop | ⅛ml | Asafoetidia - 10 gm | Copper Amino Acid Chelate 20% - | VIT C - 15 gm | |
| Juniper | ⅛ml | Caraway Ground - 10 gm | 15 gm | VIT E D - Alpha | |
| Lavender | ⅛ml | Chilli Powder - 10 gm | Garlic - 5 gm | Tocapherol - 10 gm | |
| Lemon Grass | ⅛ml | Coconut Cream Block - 10 gm | Inositol 25 gm | | |
| Mountain Savoury | ⅛ml | Coriander- 10 gm | Iron Gluconate 12.5% - 10 gm | | |
| Niaouli | ⅛ml | Dill Seeds - 10 gm | Mineral Clay Powders - 15 gm | | |
| Rose Geranium | ⅛ml | Fenugreek- 10 gm | Zinc Amino Acid Chelate 20% - | | |
| Rosemary | ⅛ml | Horseradish Ribbled - 10 gm | 5 gm | | |
| Tagestes | ⅛ml | Mace Ground - 10 gm | | | |
| Thyme Red | ⅛ml | Mustard Seed Yellow - 10 gm | | | |
| Ylang Ylang | ⅛ml | Orris Root - 10 gm | | | |

PRODUCT FORMULA BY AILMENT & ILLNESS
Product Formula V
- 2 capsules 3 times daily over 20 days
**Followed by Formula F - Clarissa Balancing System
- 2 sessions with Aromatherapist/Reflexologist
(minimum 2 hours apart, maximum 7 days apart)
**Abuse (long term)
**Trauma/shock (long term)
**Bereavement/Loss

| Essential Oils | | Herbs/Spices | Base Ingredients | | Flavouring |
|---|---|---|---|---|---|
| Bergamot | ⅛ml | Herbs: 5:1 | Honey Products | Aloe Vera/Amino | Honey - 20 ml |
| Chamomile German | ⅛ml | Chi Shao Yao - 2 gm | Royal Jelly - 3:1 - 7 gm | Acids/Vitamins | Indian Brandee - 20 ml |
| Chamomile Maroc | ⅛ml | Da Huang - 2 gm | Bee Propolis - 4:1 - 5 gm | Aloe Vera: | Vanilla - 50 gm |
| Chamomile Roman | ⅛ml | Er Cha - 2 gm | | Over 70 nutrients - ¾liter | |
| Cinnamon Leaf | ⅛ml | Qiang Huo - 2 gm | Enzymes/Minerals | Amino Acids: | |
| Clove Buds | ⅛ml | Su Mu - 2 gm | Enzymes: | L-Threonine - 15 gm | |
| Eucalyptus Globulus | ⅛ml | Ting Li Zi - 2 gm | Vegetable Enzymes - 15 gm | Superoxide Dismutase (S.O.D.) - 15 gm | |
| Fennel | ⅛ml | Wu Jia Pi - 2 gm | | | |
| Frankincense | ⅛ml | Spices: | | | |
| Hyssop | ⅛ml | Allspice - 10 gm | Minerals: | Vitamins: | |
| Juniper | ⅛ml | Asafoetidia - 10 gm | Calcium Amino Acid | VIT C - 15 gm | |
| Lemon Grass | ⅛ml | Celery Salt - 10 gm | Chelate 20% - 10 gm | VIT E D - Alpha Tocapherol - 10 gm | |
| Mountain Savoury | ⅛ml | Chilli Powder - 10 gm | Copper Amino Acid | | |
| Niaouli | ⅛ml | Coconut Cream Block - 10 gm | Chelate 20% - 15 gm | | |
| Patchouli | ⅛ml | Coconut Ground - 10 gm | Garlic - 5 gm | | |
| Rose Geranium | ⅛ml | Coriander - 10 gm | Inositol 25 gm | | |
| Rosemary | ⅛ml | Fenugreek - 10 gm | Iron Gluconate 12.5% - 10 gm | | |
| Thyme Red | ⅛ml | Horseradish Ribbled - 10 gm | Mineral Clay Powders - 15 gm | | |
| Ylang Ylang | ⅛ml | Mace Ground - 10 gm | Zinc Amino | | |
| | | Mango Powder - 10 gm | Acid Chelate 20% - 5 gm | | |

PRODUCT FORMULA BY AILMENT & ILLNESS
Product Formula W1
WEIGHT MANAGEMENT
Clarissa Weight Care System
- 2 capsules daily at bedtime over 20 days

| Essential Oils | | Herbs/Spices | Base Ingredients | | Flavouring |
|---|---|---|---|---|---|
| Bergamot | ⅛ml | Herbs: 5:1 | Honey Product | Aloe Vera/Amino Acids/Vitamins | Honey - 20 ml |
| | | Guo Teng - 2 gm | Royal Jelly - 3:1 - 1 gm | Aloe Vera: | Indian Brandee - 20 ml |
| | | Ji Xue Teng - 2 gm | Bee Propolis - 4:1 - 5 gm | Over 70 nutrients - ¾liter | Vanilla - 50 gm |
| | | Spices: | Enzymes/Minerals | Amino Acids: | |
| | | Carob - 10 gm | Enzymes: | L- Threonine - 15 gm | |
| | | Dill Seeds - 10 gm | Vegetable Enzymes - 15 gm | Superoxide Dismutase (S.O.D.) - 15 gm | |
| | | Juniper Berries - 10 gm | | | |
| | | Mixed Spices Sweet - 10 gm | Minerals: | | |
| | | | Calcium Amino Acid Chelate 20% - 10 gm | Vitamins: | |
| | | | Copper Amino Acid Chelate 20% - 15 gm | VIT C- 15 gm | |
| | | | Garlic - 5 gm | VIT E D - Alpha Tocapherol - 10 gm | |
| | | | Inositol 25 gm | | |
| | | | Iron Gluconate 12.5% - 10 gm | | |
| | | | Mineral Clay Powders - 15 gm | | |
| | | | Zinc Amino Acid Chelate 20% - 5 gm | | |

PRODUCT FORMULA BY AILMENT & ILLNESS
Product Formula W2
WEIGHT MANAGEMENT
Clarissa Meal Replacement Diet Juice - 50 ml per Meal Replacement over 20 days

| Essential Oils | | Herbs/Spices | Base Ingredients | | Flavouring |
|---|---|---|---|---|---|
| Bergamot | ⅛ml | Herbs: 5:1<br>Gao Ben - 2 gm<br>Sang Ye - 2 gm<br>Spices:<br>Dill Seeds - 10 gm<br>Fennel - 10 gm<br>Mixed Spices Sweet - 10 gm<br>Mushroom - 10 gm | Honey Products<br>Royal Jelly - 3:1 - 7 gm<br>Bee Propolis - 4:1 - 5 gm<br>Enzymes/Minerals<br>Enzymes:<br>Vegetable Enzymes - 15 gm<br>Soya Isolate - 20 gm<br>Soya Protein Isolate - 50 gm<br>Whey Protein - 20 gm<br><br>Minerals:<br>Calcium Amino Acid Chelate 20% - 10 gm<br>Copper Amino Acid Chelate 20% - 15 gm<br>Garlic - 5 gm<br>Inositol 25 gm<br>Iron Gluconate 12.5% - 10 gm<br>Mineral Clay Powders - 15 gm<br>Zinc Amino Acid Chelate 20% - 5 gm | Aloe Vera/Amino Acids/Vitamins<br>Aloe Vera:<br>Over 70 nutrients - ¾liter<br>Amino Acids:<br>L-Threonine - 15 gm<br>Superoxide Dismutase (S.O.D.) - 15 gm<br><br>Vitamins:<br>VIT C - 15 gm<br>VIT E D<br>- Alpha Tocapherol - 10 gm | Honey - 20 ml<br>Indian Brandee - 20 ml<br>Vanilla - 50 gm |

PRODUCT FORMULA BY AILMENT & ILLNESS
Product Formula W3
WEIGHT MANAGEMENT
Clarissa Chinese Slimming and Detoxifying Tea - 1 cup 3 times daily
Stale Breath

| Essential Oils | | Herbs/Spices | Flavouring | Other |
|---|---|---|---|---|
| Bergamot | ⅛ml | Herbs:.5:1<br>Bai Guo Ye (Ginkgo) - 2 gm<br>Ban Xia 2 gm<br>Chan Tiu - 2 gm<br>Chi Shao Yao - 2 gm<br>Garcinia Cambogia - 10 gm<br>Gou Teng - 2 gm<br>Horsetail - 5 gm (1:1)<br>Lian Zi (Red) - 2 gm<br>MatéLeaf- 5 gm (1:1)<br>Mao Zhao Cao (Cats Claw) 5 gm (1:1)<br>Milk Thistle Seed - 5 gm (1:1)<br>Ou Jie - 2 gm<br>Spirulina - 5 gm (1:1)<br>Wang Bu Liu Xing Guo - 2 gm<br>Wu Jia Pi - 2 gm<br>Spices:<br>Allspice - 10 gm<br>Cardamom - 10 gm<br>Cassia - 10 gm<br>Dill Seeds - 10 gm<br>Celery Salt - 10 gm<br>Garlic - 10 gm<br>Lemon Grass - 10 gm<br>Mixed Spices Sweet - 10 gm<br>Tamarind Block - 10 gm | Lemon - 20 gm | Citrin - 5 gm |

PRODUCT FORMULA BY AILMENT & ILLNESS

Product Formula W4
WEIGHT MANAGEMENT
Anti-Cellulite Formula
- 2 capsules 3 times daily over 20 days

| Essential Oils | | Herbs/Spices | Base Ingredients | | Flavouring |
|---|---|---|---|---|---|
| Aniseed: | ⅛ml | Herbs: 5:1 | Honey Products | Aloe Vera/Amino Acids/Vitamins | Honey 20 ml |
| Chamomile Maroc | ⅛ml | Dang Gui - 2 gm (Dong Quai) | Royal Jelly - 3:1 - 7 gm | Aloe Vera: | Indian Brandee - 20 ml |
| Grapeseed | ⅛ml | Guo Teng - 2 gm | Bee Propolis - 4:1 - 5 gm | Over 70 nutrients - ¾liter | Vanilla - 50 gm |
| Juniper | ⅛ml | Qiang Huo - 2 gm | | Amino Acids: | |
| | | Tian Nan Xing - 2 gm | Enzymes/Minerals | L-Threonine - 15 gm | |
| | | Wang Bu Liu Xing Guo - 2 gm | Enzymes: | Superoxide Dismutase (S.O.D.) - 15 gm | |
| | | Wu Jia Pi - 2 gm | Vegetable Enzymes - 15 gm | | |
| | | | Minerals: | Vitamins: | |
| | | Spices: | Calcium Amino Acid Chelate 20% - 10 gm | VIT C - 15 gm | |
| | | Allspice - 10 gm | Copper Amino Acid Chelate 20% - 15 gm | VIT E D - Alpha Tocapherol - 10 gm | |
| | | Cinnamon - 10 gm | Garlic - 5 gm | | |
| | | Fenugreek - 10 gm | Inositol 25 gm | | |
| | | Garlic - 10 gm | Iron Gluconate 12.5% - 10 gm | | |
| | | | Mineral Clay Powders - 15 gm | | |
| | | | Zinc Amino Acid Chelate 20% - 5 gm | | |

Product Formula XI
SKIN CARE
Bodycare Lotion

| Aloe Vera | Essential Oils | | Herbs/Spices | Honey Products | Vitamins/Amino Acids | Base Formulation |
|---|---|---|---|---|---|---|
| Bee Propolis Creme 1 ml | Benzoin | ⅛ml | Herbs: 5:1 | Bee Propolis - 4:1 - 5 gm | VIT E - 30 gm | Avocado Oil 15% |
| | Bergamot | ⅛ml | Chuan Lian Zi - 2 gm | | Euxyl K100 - 10 mg | Cellulose 15% |
| | Chamomile Maroc | ⅛ml | Da Zao - 2 gm | | Inositol - 10 mg | Colloidal Sulphur 5% |
| | Cypress | ⅛ml | | | L-Phenylaline - 10 mg | Emulsifying Ointment 30% |
| | Dill | ⅛ml | | | | P. Chloro M. Cresol 15% |
| | Hyssop | ⅛ml | | | | Purified Water 69% |
| Nectar | Lavender | ⅛ml | | | | Phenoxyethanol 1% |
| Nutritional | Patchouli | ⅛ml | Spices: | | | Sodium Laureth 5% |
| Drink | Rose Geranium | ⅛ml | Allspice - 10 gm | | | Wheatgerm Oil 15% |
| 10 ml daily | Sandlewood | ⅛ml | Cayenne Pepper - 10 gm | | | Witch Hazel Extract 15% |
| | Ylang Ylang | ⅛ml | | | | |

PRODUCT FORMULA BY AILMENT & ILLNESS
SKIN CARE

| Aloe Vera | Essential Oils | | Herbs/Spices | Honey Products | Vitamins/Amino Acids | Base Formulation |
|---|---|---|---|---|---|---|

Product Formula X2
Facecare Lotion

| Aloe Vera | Essential Oils | | Herbs/Spices | Honey Products | Vitamins/Amino Acids | Base Formulation |
|---|---|---|---|---|---|---|
| Bee Propolis Creme 1 ml | Bergamot | ⅛ml | Herbs: 5:1 | Bee Propolis - 4:1 - 5 gm | VIT E -30 gm | Emulsifying Ointment 30% |
| | Fennel | ⅛ml | Chuan Lian Zi - 2 gm | | Euxyl K100 - 10 mg | Grapeseed Oil 15% |
| | Frankincense | ⅛ml | Suan Zao Ren - 2 gm | | Inositol - 10 mg | Purified Water 69% |
| | Hyssop | ⅛ml | | | L-Phenylaline - 10 mg | Phenoxyethanol 1% |
| Nectar | Juniper | ⅛ml | Spices: | | | Vegetable Oil 15% |
| Nutritional | Lavender | ⅛ml | Aniseed - 10 gm | | | Wheatgerm Oil 15% |
| Drink | Lemon | ⅛ml | Cumin - 10 gm | | | |
| 10 ml daily | Niaouli | ⅛ml | | | | |
| | Patchouli | ⅛ml | | | | |
| | Pine | ⅛ml | | | | |
| | Rosemary | ⅛ml | | | | |

Product Formula X3
Haircare Lotion & Restoration

| Aloe Vera | Essential Oils | | Herbs/Spices | Honey Products | Vitamins/Amino Acids | Base Formulation |
|---|---|---|---|---|---|---|
| Bee Propolis Creme 1 ml | Benzoin | ⅛ml | Herbs: 5:1 | | VIT E - 30 gm | Dehydol 10% |
| | Bergamot | ⅛ml | Bo He - 2 gm | | Inositol - 10 mg | Emulsifying Ointment |

-continued

PRODUCT FORMULA BY AILMENT & ILLNESS
SKIN CARE

| Aloe Vera | Essential Oils | | Herbs/Spices | Honey Products | Vitamins/Amino Acids | Base Formulation |
|---|---|---|---|---|---|---|
| | Chamomile Maroc | ⅛ml | Da Zao - 2 gm | | L-Phenylaline - 10 gm | 30% |
| | Eucalyptus Globulus | ⅛ml | | | | Jojoba Oil 30% |
| Nectar | Jojoba | ⅛ml | Spices: | | | Purified Water 69% |
| Nutritional | Lavender | ⅛ml | Arrowroot - 10 gm | | | Phenoxyethanol 1% |
| Drink | Rose Geranium | ⅛ml | Cassia - 10 gm | | | |
| 10 ml daily | Rosemary | ⅛ml | | | | |

PRODUCT FORMULA BY AILMENT & ILLNESS
SKIN CARE

| Aloe Vera | Essential Oils | | Herbs/Spices | Honey Products | Vitamins/Amino Acids | Base Formulation |
|---|---|---|---|---|---|---|
| | | | Product Formula X4 Nutriolcare Protection Lotion | | | |
| Bee Propolis | Bergamot | ⅛ml | Herbs: 5:1 | Bee Propolis - 4:1–5 gm | VIT E - 30 gm | Avocado Oil 15% |
| Creme 1 ml | Cedarwood | ⅛ml | Chuan Lian Zi - 2 gm | | Euxyl K100 - 10 gm | Carrot Oil 15% |
| | Chamomile Maroc | ⅛ml | Hua Jiao - 2 gm | | Inositol - 10 gm | Cellulose 15% |
| | Cypress | ⅛ml | | | L-Phenylaline - 10 gm | Colloidal Sulphur 5% |
| Nectar | Fennel | ⅛ml | Spices: | | | Emulsifying Ointment |
| Nutritional | Frankincense | ⅛ml | Celery Salt - 10 g | | | 30% |
| Drink | Juniper | ⅛ml | | | | Grapeseed Oil 1.5% |
| 10 ml daily | Lavender | ⅛ml | | | | P. Chloro M. Cresol 15% |
| | Lemon | ⅛ml | | | | Purified Water 69% |
| | Mountain Savoury | ⅛ml | | | | Sodium Laureth 5% |
| | Neroli | ⅛ml | | | | Triethanolomine 10% |
| | Rose Geranium | ⅛ml | | | | Wheatgerm Oil 15% |
| | Sandlewood | ⅛ml | | | | |
| | | | Product Formula X5 | | | |
| | | | Suncare Lotion - Pre sunbathing    X5 (i) | | | |
| | | | After sun    X5 (ii) | | | |
| X5 (i) | Bergamot | ⅛ml | Herbs: 5:1 | Bee Propolis - 4:1 - 5 gm | VIT E - 30 gm | Emulsifying Ointment |
| Bee Propolis | Chamomile Maroc | ⅛ml | Cang Er Zi - 2 gm | | Euxyl K100 - 10 gm | 30% |
| Creme 1 ml | | | Qiang Huo - 2 gm | | L-Phenylaline - 10 gm | Purified Water 69% |
| | | | Spices: | | | Phenoxyethanol 1% |
| | | | Chilli - 10 gm | | | |
| | | | Garlic - 10 gm | | | |
| X5 (ii) | Bergamot | ⅛ml | Herbs: 5:1 | Bee Propolis - 4:1 - 5 gm | VIT E - 30 gm | Emulsifying Ointment |
| Bee Propolis | Dill | ⅛ml | Cang Er Zi - 2 gm | | Euxyl K100 - 10 gm | 30% |
| Creme 1 ml | Fennel | ⅛ml | Hua Jiao - 2 gm | | L-Phenylaline - 10 gm | Purified Water 69% |
| | | | Qiang Huo - 2 gm | | | Phenoxyethanol 1% |
| | | | Spices: | | | |
| | | | Cinnamon - 10 gm | | | |
| | | | Fenugreek - 10 gm | | | |

PRODUCT FORMULA BY AILMENT & ILLNESS
PET, VETERINARY & EQUINE CARE
Product Formula Y1
Immune System
Nutritional Supplement - Daily dose of 5 ml in food

| Essential Oils | | Herbs/Spices | Base Ingredients | | Flavouring |
|---|---|---|---|---|---|
| Basil | ⅛ml | Herbs: 5:1 | Honey Products | Aloe Vera/Amino | Honey - 20 ml |
| Bergamot | ⅛ml | Bai Guo Ye (Ginkgo) - 1 gm | Royal Jelly - 3:1 - 7 gm | Acids/Vitamins | Indian Brandee - |
| Camphor | ⅛ml | Ban Xia - 1 gm | Bee Propolis - 4:1 - 5 gm | Aloe Vera: | 20 ml |
| Chamomile German | ⅛ml | *Boswellia serrata* - 5 gm | | Over 70 nutrients including all | Vanilla - 50 gm |
| Chamomile Maroc | ⅛ml | Da Huang - 1 gm | Enzymes: | vitamins B1–B16 - ¾liter | |
| Chamomile Roman | ⅛ml | Er Cha - 1 gm | Co Enzyme Q10 - 10 mcg | Amino Acids: | |
| Cinnamon Leaf | ⅛ml | Gou Qi Zi (Lycium) - 1 gm | Vegetable Enzymes 4:1 - 7.5 gm | Hesperidin Complex - 7.5 gm | |
| Clove Buds | ⅛ml | Grapeseed - 15 mcg | | Histidine - 7.5 gm | |

-continued

PRODUCT FORMULA BY AILMENT & ILLNESS
PET, VETERINARY & EQUINE CARE
Product Formula Y1
Immune System
Nutritional Supplement - Daily dose of 5 ml in food

| Essential Oils | | Herbs/Spices | Base Ingredients | | Flavouring |
|---|---|---|---|---|---|
| Dill | 1/8ml | Mao Zhao Cao (Cats Claw) - 1 gm | Minerals: | Isoleucine - 7.5 gm | |
| Eucalyptus Globulus | 1/8ml | Pycnogenol - 10 mcg | Calcium Amino Acid Chelate 20% 20% - 5 gm | L-Aspartic Acid - 7.5 gm | |
| Fennel | 1/8ml | Salix Alba (White Willow) - 5 gm | Copper Amino Acid Chelate 20% - 7.5 gm | L-Glutamim - 15 gm | |
| Frankincense | 1/8ml | 1:1 | Chromium Niacin - 10 mcg | L-Phenylalenine - 7.5 gm | |
| Hyssop | 1/8ml | Shiu Niu Jiao Si - 1 gm | Devils Claw - 7.5 gm | Lecithin - 7.5 gm | |
| Juniper | 1/8ml | Su Mu - 1 gm | Garlic - 5 gm | Lecithin - 7.5 gm | |
| Lemon Grass | 1/8ml | Wu Jia Pi - 1 gm | Inositol 12.5 gm | L-Taurine - 7.5 gm | |
| Mountain Savoury | 1/8ml | | Iron Gluconate 12.5% - 5 gm | L-Threonine - 7.5 gm | |
| Niaouli | 1/8ml | Spices: | Magnesium Amino Acid Chelate - 10 gm | Phosphatidyl Choline - 10 gm | |
| Peppermint | 1/8ml | Allspice - 10 gm | Maganese Gluconate - 10 gm | | Vitamins: |
| Rose Geranium | 1/8ml | Asafoetidia - 10 gm | Mineral Clay Powders - 7.5 gm | Betacorotene Dunaliella Salina Algae 2.5% - 7.5 gm | |
| Rosemary | 1/8ml | Chilli Powder- 10 gm | Molybdenum - 7.5 gm | Biotin - 5 mcg | |
| Tagestes | 1/8ml | Cinnamon Sugar - 10 gm | Selenium Methionine 5% - 5 gm | Folic Acid - 16 gm | |
| Thyme Red | 1/8ml | Coconut Cream Block - 10 gm | Superoxide Dismutase (S.O.D.) - 7.5 gm | VIT C - 15 gm | |
| Ylang Ylang | 1/8ml | Coriander - 10 gm | Zinc Amino Acid Chelate 20% - 2.5 gm | VIT E D - Alpha Tocapherol - 10 gm | |
| | 1/8ml | Fenugreek - 10 gm | Nutritional Oils & Fats | K1 5% - 1 gm | |
| | | Horseradish Ribbled - 10 gm | Cod Liver Powder - 7.5 gm | | |
| | | Juniper Berries - 10 gm | Evening Primrose - 15 ml | | |
| | | Laos - 10 gm | Linoleic Acid - 7.5 gm | | |
| | | Mace Ground - 10 gm | Linolenic Acid - 7.5 gm | | |

PRODUCT FORMULA BY AILMENT & ILLNESS
PET, VETERINARY & EQUINE CARE
6 capsules daily in food over 20 days
Product Formula Y2
Intestine System

| Essential Oils | | Herbs/Spices | Base Ingredients | | Flavouring |
|---|---|---|---|---|---|
| Aniseed | 1/8ml | Herbs: 5:1 | Honey Products | Aloe Vera/Amino Acids/Vitamins | Honey - 20 ml |
| Bergamot | 1/8ml | Bal Guo Ye (Ginkgo) - 2 gm | Royal Jelly - 3:1 - 7 gm | Aloe Vera: | Indian Brandee - 20 ml |
| Camphor | 1/8ml | Da Huang - 2 gm | Bee Propolis - 4:1 - 5 gm | Over 70 nutrients - 3/4 liter | Vanilla - 50 gm |
| Chamomile German | 1/8ml | Er Cha - 2 gm | | Amino Acids: | |
| Chamomile Maroc | 1/8ml | Salix Alba (White Willow) - 10 gm | Enzymes/Minerals | L-Threonine - 15 gm | |
| Chamomile Roman | 1/8ml | 1:1 | Enzymes: | Superoxide Dismutase (S.O.D.) - 25 gm | |
| Cinnamon Leaf | 1/8ml | Shiu Niu Jiao Si - 2 gm | Vegetable Enzymes - 15 gm | | |
| Clove Buds | 1/8ml | Su Mu - 2 gm | | | |
| Eucalyptus Globulus | 1/8ml | Wu Jia Pi - 2 gm | Minerals: | | |
| Fennel | 1/8ml | | Calcium Amino Acid Chelate 20% - 10 gm | Vitamins: | |
| Frankincense | 1/8ml | Spices: | Copper Amino Acid Chelate 20% - 15 gm | VIT C - 15 gm | |
| Ginger | 1/8ml | Asafoetidia - 10 gm | Garlic - 5 gm | VIT E D - Alpha Tocapherol - 10 gm | |
| Hyssop | 1/8ml | Cassia - 10 gm | Inositol 25 gm | | |
| Juniper | 1/8ml | Chilli Powder - 10 gm | Iron Gluconate 12.5% - 10 gm | | |
| Lemon Grass | 1/8ml | Coconut Cream Block - 10 gm | Mineral Clay Powders - 15 gm | | |
| Mountain Savoury | 1/8ml | Coriander - 10 gm | Zinc Amino Acid Chelate 20% - 5 gm | | |
| Niaouli | 1/8ml | Cream of Tartar- 10 gm | | | |
| Peppermint | 1/8ml | Dill Seeds - 10 gm | | | |
| Rose Geranium | 1/8ml | Fenugreek - 10 gm | | | |
| Rosemary | 1/8ml | Horseradish Ribbled - 10 gm | | | |
| Tagestes | 1/8ml | Mace Ground - 10 gm | | | |
| Thyme Red | 1/8ml | | | | |
| Ylang Ylang | 1/8ml | | | | |

PRODUCT FORMULA BY AILMENT & ILLNESS
PET, VETERINARY & EQUINE CARE
6 capsules daily days in food over 20 days
Product Formula Y3
Depression

| Essential Oils | | Herbs/Spices | Base Ingredients | | Flavouring |
|---|---|---|---|---|---|
| Basil | ⅛ml | Herbs: 5:1 | Honey Products | Aloe Vera/Amino | Honey 20 ml |
| Bergamot | ⅛ml | Bai Guo Ye (Ginkgo) - 2 gm | Royal Jelly - 3:1 - 7 gm | Acids/Vitamins | Indian Brandee - |
| Camphor | ⅛ml | Da Huang 2 gm | Bee Propolis - 4:1 - 5 gm | Aloe Vera: | 20 ml |
| Chamomile German | ⅛ml | Er Cha - 2 gm | | Over 70 nutrients - | Vanilla 50 gm |
| Chamomile Maroc | ⅛ml | Su Mu - 2 gm | Enzymes/Minerals | ¾liter | |
| Chamomile Roman | ⅛ml | Wu Jia Pi - 2 gm | Enzymes: | Amino Acids: | |
| Cinnamon Leaf | ⅛ml | | Vegetable Enzymes - 15 gm | L-Threonine 15 gm | |
| Clove Buds | ⅛ml | Spices: | | Superoxide Dismutase | |
| Dill | ⅛ml | Asafoetidia - 10 gm | Minerals: | (S.O.D.) - | |
| Eucalyptus Globulus | ⅛ml | Chilli Powder - 10 gm | Calcium Amino Acid Chelate 20% - | 15 gm | |
| Fennel | ⅛ml | Coconut Cream Block - 10 gm | 10 gm | Vitamins: | |
| Frankincense | ⅛ml | Coriander - 10 gm | Copper Amino Acid Chelate 20% - | VIT C - 15 gm | |
| Hyssop | ⅛ml | Cumin - 10 gm | 15 gm | VIT E D - Alpha | |
| Juniper | ⅛ml | Fenugreek - 10 gm | Garlic - 5 gm | Tocapherol - 10 gm | |
| Lavender | ⅛ml | Horseradish Ribbled - 10 gm | Inositol 25 gm | | |
| Lemon Grass | ⅛ml | Juniper Berries - 10 gm | Iron Gluconate 12.5% - 10 gm | | |
| Mountain Savoury | ⅛ml | Mace Ground - 10 gm | Mineral Clay Powders - 15 gm | | |
| Niaouli | ⅛ml | Nutmeg - 10 gm | Zinc Amino Acid Chelate 20% - | | |
| Peppermint | ⅛ml | | 5 gm | | |
| Rose Geranium | ⅛ml | | | | |
| Rosemary | ⅛ml | | | | |
| Tagestes | ⅛ml | | | | |
| Thyme Red | ⅛ml | | | | |
| Ylang Ylang | ⅛ml | | | | |

PRODUCT FORMULA BY AILMENT & ILLNESS
PET, VETERINARY & EQUINE CARE
6 capsules daily in food over 20 days
Product Formula Y4
Viral Antidote

| Essential Oils | | Herbs/Spices | Base Ingredients | | Flavouring |
|---|---|---|---|---|---|
| Basil | ⅛ml | Herbs: 5:1 | Honey Products | Aloe Vera/Amino | Honey - 20 ml |
| Bergamot | ⅛ml | Bai Guo Ye (Ginkgo) - 2 gm | Royal Jelly - 3:1 - 7 gm | Acids/Vitamins | Indian Brandee - |
| Camphor | ⅛ml | Da Huang - 2 gm | Bee Propolis - 4:1 - 5 gm | Aloe Vera: | 20 ml |
| Chamomile German | ⅛ml | Er Cha - 2 gm | | Over 70 nutrients - | Vanilla - 50 gm |
| Chamomile Maroc | ⅛ml | Mao Zhao Cao (Cats Claw) - 2 gm | Enzymes/Minerals | ¾liter | |
| Chamomile Roman | ⅛ml | Salix Alba (White Willow) - 10 gm | Enzymes: | Amino Acids: | |
| Cinnamon Leaf | ⅛ml | 1:1 | Vegetable Enzymes - 15 gm | L-Glutamim 15 gm | |
| Clove Buds | ⅛ml | Shiu Niu Jiao Si - 2 gm | | L-Threonine - 15 gm | |
| Eucalyptus Globulus | ⅛ml | Su Mu - 2 gm | Minerals: | Superoxide Dismutase | |
| Fennel | ⅛ml | Wu Jia Pi - 2 gm | Calcium Amino Acid Chelate 20% - | (S.O.D.) - 15 gm | |
| Frankincense | ⅛ml | Zhi Zi - 2 gm | 10 gm | | |
| Ginger | ⅛ml | | Copper Amino Acid Chelate 20% - | | |
| Hyssop | ⅛ml | Spices: | 15 gm | Vitamins: | |
| Juniper | ⅛ml | Allspice - 10 gm | Garlic - 5 gm | VIT C - 15 gm | |
| Lemon Grass | ⅛ml | Asafoetidia - 10 gm | Inositol 25 gm | VIT E D - Alpha | |
| Mountain Savoury | ⅛ml | Celery Salt - 10 gm | Iron Gluconate 12.5% - 10 gm | Tocapherol - 10 gm | |
| Niaouli | ⅛ml | Chilli Powder - 10 gm | Mineral Clay Powders - 15 gm | | |
| Peppermint | ⅛ml | Coconut Cream Block - 10 gm | Zinc Amino Acid Chelate 20% - | | |
| Rose Geranium | ⅛ml | Coriander - 10 gm | 5 gm | | |
| Rosemary | ⅛ml | Cream of Tartar - 10 gm | | | |
| Tagestes | ⅛ml | Fenugreek - 10 gm | | | |
| Thyme Red | ⅛ml | Horseradish Ribbled - 10 gm | | | |
| Ylang Ylang | ⅛ml | Mace Ground - 10 gm | | | |
| | ⅛ml | Mixed Spices Sweet - 10 gm | | | |

PRODUCT FORMULA BY AILMENT & ILLNESS
2 sessions with Aromatherapist/Reflexologist
(minimum 2 hours apart maximum 7 days apart)
Clarissa Recovery Remedy

| Essential Oils | | Herbs/Spices | Base Ingredients | Carrier Oils |
|---|---|---|---|---|
| | | Product Formula Z - CRA | | |
| | | Meningitis | | |
| | | Strokes & Heart Attacks | | |
| Basil | ⅛ml | Herbs: 5:1 | Aloe Vera Pure - 20 ml | Avocado - 10 ml |
| Carrot | ⅛ml | Chan Tiu - 2 gm | Honey - 20 ml | Grapeseed - 40 ml |
| Ginger | ⅛ml | Chen Xiang - 2 gm | Hazelnut - 10 ml | |
| | | Fu Pen Zi - 2 gm | | |
| | | Qiang Huo - 2 gm | | |
| | | Shu Di Huang - 2 gm | | |
| | | Spices: | | |
| | | Anise Star - 10 gm | | |
| | | Cumin - 10 gm | | |
| | | Product Formula Z - CRB | | |
| | | Irritable Bowel | | |
| | | Organophosphate Disease (OP's) | | |
| Aniseed | ⅛ml | Herbs: 5:1 | Aloe Vera Pure - 20 ml | Avocado - 10 ml |
| Basil | ⅛ml | Bai He - 2 gm | Honey - 20 ml | Grapeseed - 40 ml |
| Bergamot | ⅛ml | Chen Xiang - 2 gm | Hazelnut - 10 ml | |
| Carrot | ⅛ml | Chi Shao Yao - 2 gm | | |
| | | Huo Ma Ren - 2 gm | | |
| | | Shu Di Huang - 2 gm | | |
| | | Spices: | | |
| | | Anise Star -10 gm | | |
| | | Cassia - 10 gm | | |

PRODUCT FORMULA BY AILMENT & ILLNESS
2 sessions with Aromatherapist/Reflexologist
(minimum 2 hours apart maximum 7 days apart)
Clarissa Recovery Remedy

| Essential Oils | | Herbs/Spices | Base Ingredients | Carrier Oils |
|---|---|---|---|---|
| | | Product Formula Z - CRC2 | | |
| | | Influenza | | |
| Basil | ⅛ml | Herbs: 5:1 | Aloe Vera Pure - 20 ml | Avocado - 10 ml |
| Bergamot | ⅛ml | Bo He - 2 gm | Honey - 20 ml | Grapeseed - 40 ml |
| Eucalyptus Globulus | ⅛ml | Cang Er Zi - 2 gm | | Hazelnut - 10 ml |
| Jojoba | ⅛ml | Chen Xiang - 2 gm | | |
| | | Da Zao - 2 gm | | |
| | | Lian Zi - 2 gm | | |
| | | Shu Di Huang - 2 gm | | |
| | | Spices: | | |
| | | Anise Star - 10 gm | | |
| | | Fennel - 10 gm | | |
| | | Product Formula Z- CRJ | | |
| | | Alzheimers Disease | | |
| | | Batten's Disease | | |
| | | Herpes | | |
| | | Parkinson's Disease | | |
| | | Senile Dimentia | | |
| Basil | ⅛ml | Herbs: 5:1 | Aloe Vera Pure - 20 ml | Avocado - 10 ml |
| Carrot | ⅛ml | Bai Gou - 2 gm | Honey - 20 ml | Grapeseed - 40 ml |
| Eucalyptus Globulus | ⅛ml | Cang Er Zi - 2 gm | | Hazelnut - 10 ml |
| | | Chen Xiang - 2 gm | | |
| | | Dan Shen - 2 gm | | |
| | | Gao Ben - 2 gm | | |
| | | Shu Di Huang - 2 gm | | |

PRODUCT FORMULA BY AILMENT & ILLNESS
2 sessions with Aromatherapist/Reflexologist
(minimum 2 hours apart maximum 7 days apart)
Clarissa Recovery Remedy
-continued

| Essential Oils | Herbs/Spices | Base Ingredients | Carrier Oils |
|---|---|---|---|
| | Spices:<br>Anise Star -10 gm<br>Coriander -10 gm | | |

PRODUCT FORMULA BY AILMENT & ILLNESS
2 sessions with Aromatherapist/Reflexologist
(minimum 2 hours apart maximum 7 days apart)
Clarissa Recovery Remedy
Product Formula Z - CRM
Anaemia
Motor Neurone Disease
M.E.
M.S.
(Muscular Dystrophy
Thyroid Gland (over & under active)

| Essential Oils | | Herbs/Spices | Base Ingredients | Carrier Oils |
|---|---|---|---|---|
| Basil | ⅛ml | Herbs: 5:1 | Aloe Vera Pure - 20 ml | Avocado - 10 ml |
| Bergamot | ⅛ml | Bai Jiang Cao - 2 gm | Honey - 20 ml | Grapeseed - 40 ml |
| Eucalyptus Globulus | ⅛ml | Chen Xiang - 2 gm | Hazelnut - 10 ml | |
| Juniper | ⅛ml | Chi Shao Yao - 2 gm | | |
| | | Shu Di Huang - 2 gm | | |
| | | Ting Li Zi - 2 gm | . | .. |
| | | Ye Tu Hua - 2 gm | | |
| | | Spices: | | |
| | | Anise Star -10 gm | | |
| | | Ginger - 10 gm | | |

PRODUCT FORMULA BY AILMENT & ILLNESS
NUTRITIONAL BOOST
2 sessions Reflexology (minimum 2 hours apart maximum 7 days apart
Clarissa Recovery Remedy
Product Formula Z - CRN
Acne
Aids
Anorexia
Bulimia
Cancer
Candida
Hepatitis
Leukaemia
Sports - Energy booster & stamina

| Essential Oils | | Herbs/Spices | | Base Ingredients | Massage Oils |
|---|---|---|---|---|---|
| Black Pepper | ⅛ml | Herbs: 5:1 | | Honey Products | Aloe Vera/Amino | Avocado - 10 ml |
| Chamomile Roman | ⅛ml | Bai Guo Ye (Ginkgo) - 2 gm | | Honey - 20 ml | Acids/Vitamins | Grapeseed - 40 ml |
| Eucalyptus Globulus | ⅛ml | Bai Ji Tian -2 gm | | Royal Jelly - 2 gm | Aloe Vera: | Hazelnut - 10 ml |
| Fatigue | ⅛ml | Che Qian Zi - 2 gm | | Bee Propolis - 3 gm | Over 70 nutri- | |
| Juniper | ⅛ml | Dang Shen - 2 gm | | | ents - 40 ml | |
| Peppermint | ⅛ml | Fu Pen Zi - 2 gm | | | Amino Acids: | |
| Tagestes | ⅛ml | He Zi - 2 gm | | Enzymes/Minerals | Histidine - 3 gm | |
| | ⅛ml | Xing Ren - 2 gm | | Enzymes: | L-Phenylalenine - 3 gm | |
| | | | | Co-Enzyme Q10 - 2 mcg | L-Threonine - 3 gm | |
| | | Spices: | | Minerals: | Vitamins: | |
| | | Arrowroot - 10 gm | | | | |

PRODUCT FORMULA BY AILMENT & ILLNESS
NUTRITIONAL BOOST 2 sessions Reflexology (minimum 2 hours apart maximum 7 days apart)
Clarissa Recovery Remedy
Product Formula Z - CRN Acne
Aids
Anorexia
Bulimia
Cancer
Candida
Hepatitis
Leukaemia
Sports - Energy booster & stamina

| Essential Oils | Herbs/Spices | Base Ingredients | | Massage Oils |
|---|---|---|---|---|
| | Ginger - 10 gm | Calcium Amino Acid Chelate 20% - 2 gm | Betacorotene Dunaliella Salina Algae - 3 gm | |
| | Laos - 10 gm | Inositol - 4 gm | Biotin - 1 mcg | |
| | Tumeric - 16 gm | Iron Gluconate 12.5% - 2 gm | VIT C - 3 gm | |
| | | Zinc Amino Acid Chelate 20% - 1 gm | VIT E D - Alpha Tocapherol - 2 gm | |
| | | | K1 - 300 mg | |
| | | Nutritional Oils | | |
| | | Evening Primrose - 5 ml | | |

PRODUCT FORMULA BY AILMENT & ILLNESS 2 sessions with Aromatherapist/Reflexologist
(minimum 2 hours apart maximum 7 days apart)
Clarissa Recovery Remedy

| Essential Oils | | Herbs/Spices | Base Ingredients | Carrier Oils |
|---|---|---|---|---|
| | | Product Formula Z - CRR | | |
| | | Arthritis - Rheumatoid | | |
| | | Osteoporosis | | |
| Basil | ⅛ml | Herbs: 5:1 | Aloe Vera Pure - 20 ml | Avocado - 10 ml |
| Bergamot | ⅛ml | Bai Jiang Cao - 2 gm | Honey - 20 ml | Grapeseed - 40 ml |
| Eucalyptus Globulus | ⅛ml | Chen Xiang - 2 gm | | Hazelnut - 10 ml |
| Juniper | ⅛ml | Chuan Lian Zi - 2 gm | | |
| Niauli | ⅛ml | Huo Ma Ren - 2 gm | | |
| | | Ou Jie - 2 gm | | |
| | | Shu Di Huang - 2 gm | | |
| | | Spices: | | |
| | | Anise Star-10 gm | | |
| | | Dill - 10 gm | | |
| | | Product Formula Z - CRS3 | | |
| | | Maintenance Recovery Massage | | |
| Basil | ⅛ml | Herbs: 5:1 | Aloe Vera Pure - 20 ml | Avocado - 10 ml |
| Bergamot | ⅛ml | Bai Dou Kou - 2 gm | Honey - 20 ml | Grapeseed - 40 ml |
| Dill | ⅛ml | Chen Xiang - 2 gm | Hazelnut - 10 ml | |
| Eucalyptus Globulus | ⅛ml | Dan Shen - 2 gm | | |
| | | Ji Xue Feng- 2 gm | | |
| | | Shu Di Huang - 2 gm | | |
| | | Spices: | | |
| | | Anise Star-10 gm | | |
| | | Cinnamon - 10 gm | | |

PRODUCT FORMULA BY AILMENT & ILLNESS
Product Formula Z - CRZ
Recovery & Toning Bath Oil (20 applications)

| Essential Oils | | Herbs/Spices | Carrier Oils |
|---|---|---|---|
| Bergamot | ⅛ml | Herbs: 5:1 | Grapeseed Oil - 40 ml |
| Lavender | ⅛ml | Cang Er Zi - 1 gm | Avocado Oil - 40 ml |
| Rosemary | ⅛ml | Chen Xiang - 1 gm | Water - 160 ml |
| | | Da Huang - 1 gm | |
| | | Shu Di Huang - 1 gm | |
| | | Ting Li Zi - 1 gm | |
| | | Spices: | |
| | | Anise Star - 1 gm | |

What is claimed is:

1. A medicinal or cosmetic composition for oral administration comprising at least one essential oil in combination with at least one spice selected from the group consisting of asapoetidia, coconut, coriander, fenugreek and horseradish; at least one herb selected frorm the group consisting of *Acacia Catechu, Acanthopanax Gracilistylus, Cacsalpinia Sappan, Epimedium Spinosa, Paeonia lactiflora, Paeonia obovata, Atractylodes macrocephala, Glycyrrhiza uralexisis, Glycyrrhiza glabra, Lycium chinense, Nauclea rhyncholphylla, Cinnainomum cassia, Astragalus membranaceus, Scutellaria baicalensis, Schizonepeta tenuifolia, Ephedra sinica, Ophiopogon japonicus, Paeonia suffruticosa, Artemisia annua, Aretemisia apiacea, Panax notoginseng, Cornus officinalis, Acorius gramineus, Reluhania glutinosa, Gastrodia elata, Asparagus cochiichinensis, Cuscuta chinensis, Schizandra chinensis, Schizandra spenanthera, Magnolia liliflora, Epimedium brevicomum, Epimedium grandiflorun, Epimedium sagittatum, Houttuynia cordata, Polygala tenuifolia*; and *Perilla frutescens*, and an Aloe Vera extract.

2. A medicinal or cosmetic composition according to claim 1, wherein the essential oil is selected from the group consisting of bergamot, chamomile german, chamomile maroc, chamomile roman, cinnamon zeylanicum, clove buds, eucalyptus globulus, frankincense, fennel, hyssop, juniper, lemon grass, mountain savory, niaouli, red thyme, rosemary, rose geranium, tagestes and ylang ylang.

3. A medicinal or cosmetic composition according to claim 1 in combination with a honey product.

4. A medicinal or cosmetic composition according to claim 1 in combination with one or more vitamins, minerals, amino acids, enzymes, flavorings and/or Bach flower remedies.

5. A tablet or capsule for oral administration comprising a medicinal or cosmetic composition according to claim 1.

6. A method for the treatment of disease or physical disability or sports injuries, for the build up and maintenance of the immune system, or for the protection against disease or pollution comprising the step of administering to a patient in need thereof an effective amount of the composition of claim 1.

7. A method for weight management comprising the step of administering to a patient in need thereof an effective amount of the composition of claim 1.

8. A medicinal or cosmetic composition according to claim 2 in combination with a honey product.

9. A medicinal or cosmetic composition according to claim 2 in combination with one or more vitamins, minerals, amino acids, enzymes, flavorings and/or Bach flower remedies.

10. A tablet or capsule for oral administration comprising a medicinal or cosmetic composition according to claim 2.

11. A method for the treatment of disease or physical disability or sports injuries, for the build up and maintenance of the immune system, or for the protection against disease or pollution comprising the step of administering to a patient in need thereof an effective amount of the composition of claim 2.

12. A method for weight management comprising the step of administering to a patient in need thereof an effective amount of the composition of claim 2.

* * * * *

UNITED STATES PATENT AND TRADEMARK OFFICE
CERTIFICATE OF CORRECTION

PATENT NO.     : 6,280,751 B1
DATED          : August 28, 2001
INVENTOR(S)    : Fletcher et al.

It is certified that error appears in the above-identified patent and that said Letters Patent is hereby corrected as shown below:

<u>Column 77,</u>
Replace claim 1 with the following:

-- 1.   A medicinal or cosmetic composition for oral administration comprising at least one essential oil in combination with at least one spice selected from the group consisting of asapoetidia, coconut, coriander, fenugreek and horseradish, at least one herb selected [frorm] <u>from</u> the group consisting of *Acacia Catechu, Acanthopanax Gracilistylus, Caesalpinia Sappan, Epimedium Spinosa, Paeonia lactiflora, Paeonia obovata, Atractylodes marocephala, Glycyrrhiza [uralexisis]* <u>uralensis</u>, *Glycyrrhiza glabra, Lycium chinense, Nauclea rhyncholphylla, [Cinnainomum]* <u>Cinnamomum</u> *cassia, Astragalus membranaceus, Scutellaria baicalensis, Schizonepeta tenuifolia, Ephedra sinica, Ophiopogon japonicus, Paeonia suffruticosa, Artemisia annua, Aretemisia apiacea, Panax notoginseng, Cornus officinalis, Acorius gramineus, [Reluhania]* <u>Rehmania</u> *glutinosa, Gastrodia elata, Asparagus [cochiichinensis]* <u>cochinchinensis</u>, *Cuscuta chinensis, Schizandra chinensis, Schizandra spenanthera, Magnolia liliflora, Epimedium [brevicomum]* <u>brevicornum</u>, *Epimedium [grandiflorun]* <u>grandiflorum</u>, *Epimedium sagittatum, Houttuynia cordata, Polygala tenuifolia,* and *Perilla frutescens,* and an Aloe Vera extract. --

Signed and Sealed this

Fourth Day of June, 2002

*Attest:*

*Attesting Officer*

JAMES E. ROGAN
*Director of the United States Patent and Trademark Office*